United States Patent
Khalil et al.

(10) Patent No.: US 6,353,226 B1
(45) Date of Patent: Mar. 5, 2002

(54) NON-INVASIVE SENSOR CAPABLE OF DETERMINING OPTICAL PARAMETERS IN A SAMPLE HAVING MULTIPLE LAYERS

(75) Inventors: Omar S. Khalil, Libertyville; Xiaomao Wu, Gurnee, both of IL (US); Johannes Sake Kanger; Rene' Alexander Bolt, both of Enschede (NL); Shu-Jen Yeh, Grayslake, IL (US); Charles F. Hanna, Libertyville, IL (US); Frits Frans Maria de Mul, Almelo (NL)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/198,094

(22) Filed: Nov. 23, 1998

(51) Int. Cl.[7] .......................... A61B 5/00; G01N 21/35; G01N 21/59
(52) U.S. Cl. .............................. 250/341.8; 250/339.11; 356/432; 600/310; 600/322; 600/323
(58) Field of Search ................ 250/341.8, 339.11; 600/310, 322, 323; 356/432

(56) References Cited

U.S. PATENT DOCUMENTS 3,638,640 A  2/1972  Shaw (List continued on next page.)

FOREIGN PATENT DOCUMENTS

| EP | 0 627 619 | 12/1994 |
| EP | 97/27800 | 8/1997 |
| EP | 0 843 986 | 5/1998 |
| WO | 9220273 | 11/1992 |
| WO | 9313706 | 7/1993 |

OTHER PUBLICATIONS

Tsuchiya, Y, et al., "Quantitation of absorbing substances in turbid media such a human tissues based on the microscopic Beer–Lambert law", Optics Communications, NL, North–Holland Publishing Co., vol. 144, No. 4–6 (1997) pp. 269–280.

(List continued on next page.)

*Primary Examiner*—Constantine Hannaher
(74) *Attorney, Agent, or Firm*—David L. Weinstein

(57) ABSTRACT

Apparatus and method for non-invasively measuring at least one optical parameter of a sample, particularly a sample of tissue that comprises a plurality of layers. The at least one parameter can be used to determine the presence or concentration of an analyte of interest in the sample of tissue. The apparatus and method of the present invention (1) measure light that is substantially reflected, scattered, absorbed, or emitted from a shallower layer of the sample of tissue, (2) measure light that is substantially reflected, scattered, absorbed, or emitted from a deeper layer of the sample of tissue, (3) determine at least one optical parameter for each of these layers, and (4) account for the effect of the shallower layer on the at least one optical parameter of the deeper layer. Specifying the sampling depth allows determinations of the optical properties of a specific layer of the sample of the tissue, e.g., dermis, and decreases interference from other layers, e. g., stratum corneum and epidermis, in these determinations.

24 Claims, 13 Drawing Sheets

U.S. PATENT DOCUMENTS

| | | | |
|---|---|---|---|
| 4,223,680 | A | 9/1980 | Jöbsis |
| 4,655,225 | A | 4/1987 | Dáhne et al. |
| 5,007,423 | A | 4/1991 | Branstetter et al. |
| 5,057,695 | A | 10/1991 | Hirao et al. |
| 5,086,229 | A | 2/1992 | Rosenthal et al. |
| 5,122,974 | A | 6/1992 | Chance |
| 5,187,672 | A | 2/1993 | Chance et al. |
| 5,237,178 | A | 8/1993 | Rosenthal et al. |
| 5,277,181 | A | 1/1994 | Mendelson et al. |
| 5,297,548 | A | 3/1994 | Pologe |
| 5,324,979 | A | 6/1994 | Rosenthal |
| 5,372,136 | A | 12/1994 | Steuer et al. |
| 5,419,321 | A | 5/1995 | Evans |
| 5,490,506 | A | 2/1996 | Takatani et al. |
| 5,492,118 | A | 2/1996 | Gratton et al. |
| 5,492,769 | A | 2/1996 | Pryor et al. |
| 5,499,627 | A | 3/1996 | Steuer et al. |
| 5,513,642 | A | 5/1996 | Ostrander |
| 5,524,617 | A | 6/1996 | Mannheimer |
| 5,551,422 | A | 9/1996 | Simonsen et al. |
| 5,553,615 | A | 9/1996 | Carim et al. |
| 5,632,273 | A | 5/1997 | Suzuki |
| 5,676,143 | A | 10/1997 | Simonsen et al. |
| 5,720,284 | A | 2/1998 | Aoyagi et al. |
| 5,770,454 | A | 6/1998 | Essenpreis et al. |
| 5,844,239 | A | * 12/1998 | Kimura .................... 250/341.8 |

OTHER PUBLICATIONS

Wilson, B. et al.,"Optical Reflectance and Transmittance of Tissues: Principles and Applications", IEEE Journal of Quantum Electronics, US, IEEE Inc., New York, vol. 26, No. 12, (1990) pp 2186–2199.

Tooke et al, "Skin Microvascular Blood Flow Control In Long Duration Diabetics With and Without Complications", Diabetes Research (1987) 5, 189–192.

S. L. Robbins et al., *Pathologic Basis of Disease*, 3$^{rd}$ Edition, W. B. Saunders Company, Philadelphia, 1984, p. 972–990.

G. S. Wilson, et al. "Progress toward the Development of an Implantable Sensor for Glucose", Clin. Chem. 38/9, 1613–1617 (1992).

L. Reynolds et al., "Diffuse reflectance from a finite blood medium: applications to the modeling of fiber optic catheters", Applied Optics, vol. 15, No. 9 (1976), pp. 2059–2067.

R. A. J. Groenhuis et al., "Scattering and absorption of turbid materials determined from reflection measurements. 1: Theory", Applied Optics, vol. 22, No. 16 (1983), pp. 2456–2462.

M. S. Patterson et al., "Quantitative reflectance spectrophotometry for the noninvasive measurement of photosensitizer concentration in tissue during photodynamic therapy", SPIE (Society for Photo–optical Instrument Engineering) Proceedings, vol. 1065 (1989), pp. 115–122.

B. Chance et al., "Effect of Solutes on Optical Properties of Biological Materials: Models, Cells, and Tissues", Analytical Biochemistry, 227, 351–362 (1995).

H. Liu et al., "Dependence of Tissue Optical Properties on Solute–Induced Changes in Refractive Index and Osmolarity", Journal of Biomedical Optics, vol. 1, No. 2, 200–211 (Apr. 1996).

J. Qu et al., "Monte Carlo Modeling Studies of the Effect of Physiological Factors and Other Analytes on the Determination of Glucose Concentration in vivo by Near Infrared Optical Absorption and Scattering Measurements", Journal of Biomedical Optics 2(3), 319–325 (Jul. 1997).

I. M. Braverman, "The Cutaneous Microcirculation: Ultrastructure and Microanatomical Organization", Microcirculation, vol. 4, No. 3 (1997) pp. 329–340.

G. Kumar et al., "Optical probe geometry for near–infrared spectroscopy of biological tissue", Applied Optics, vol. 36, No. 10 (Apr. 1, 1997), pp. 2286–2293.

W. Steenbergen et al., "New optical tissue phantom and its use for studying laser Doppler blood flowmetry", SPIE Proceedings, vol 3196 (1997), pp. 12–23.

R. Graaff et al., "Reduced light–scattering properties for mixtures of spherical particles: a simple approximation derived from Mie calculations", Applied Optics, vol. 31, No. 10 (Apr. 1, 1992), pp. 1370–1376.

Co–pending U.S. application Ser. No. 09/080,470, filed May 18, 1998.

* cited by examiner

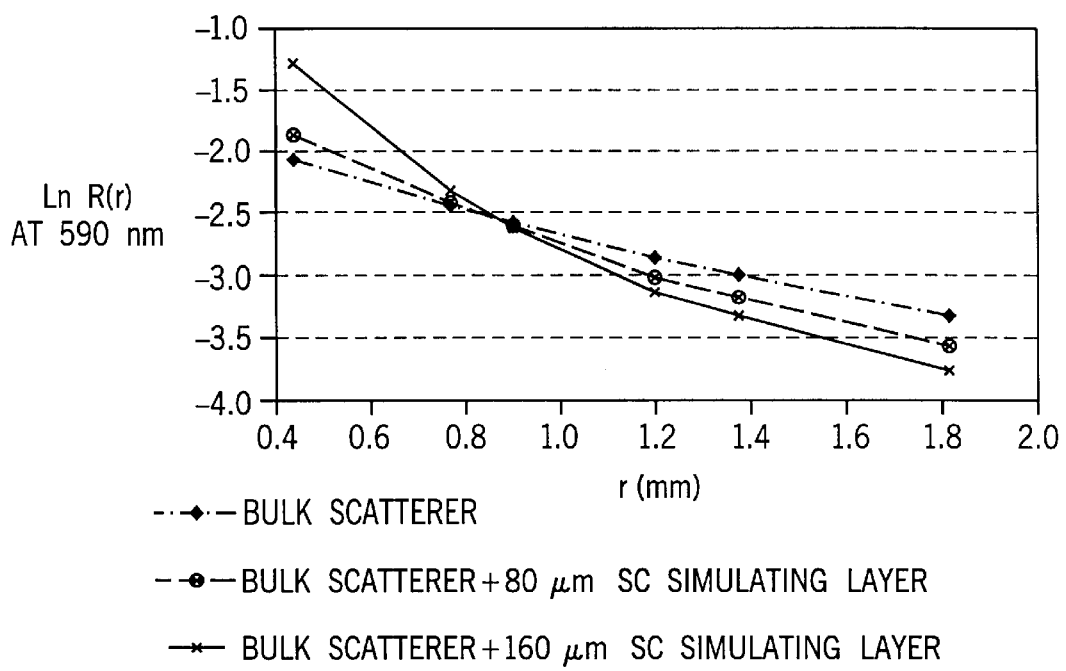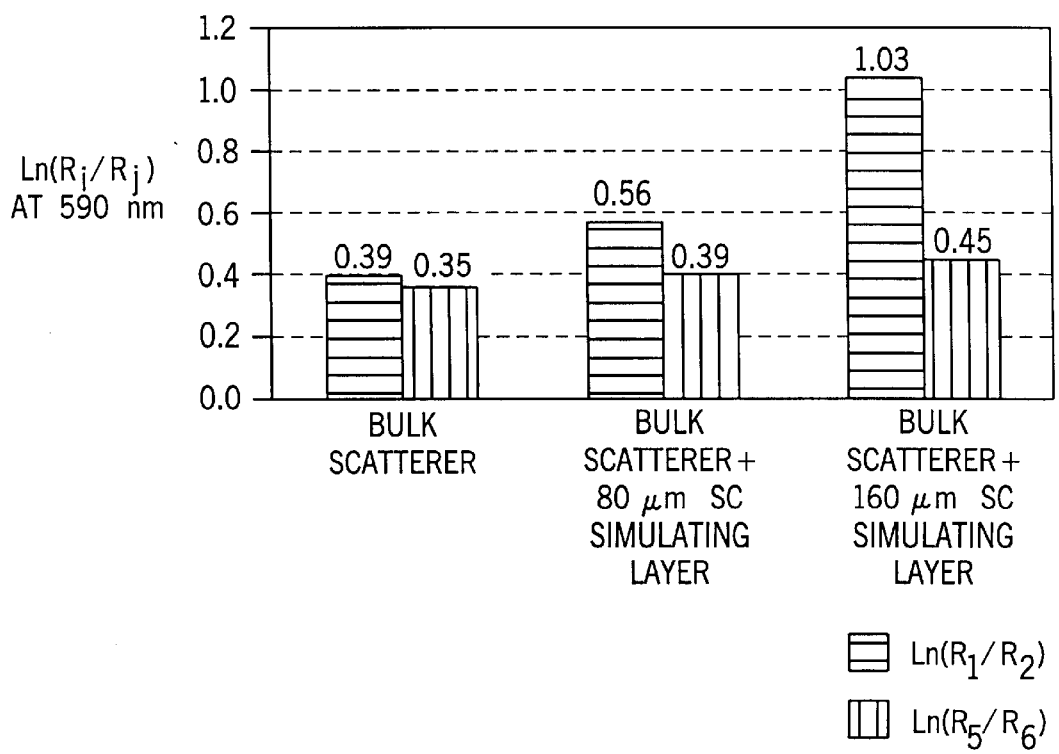

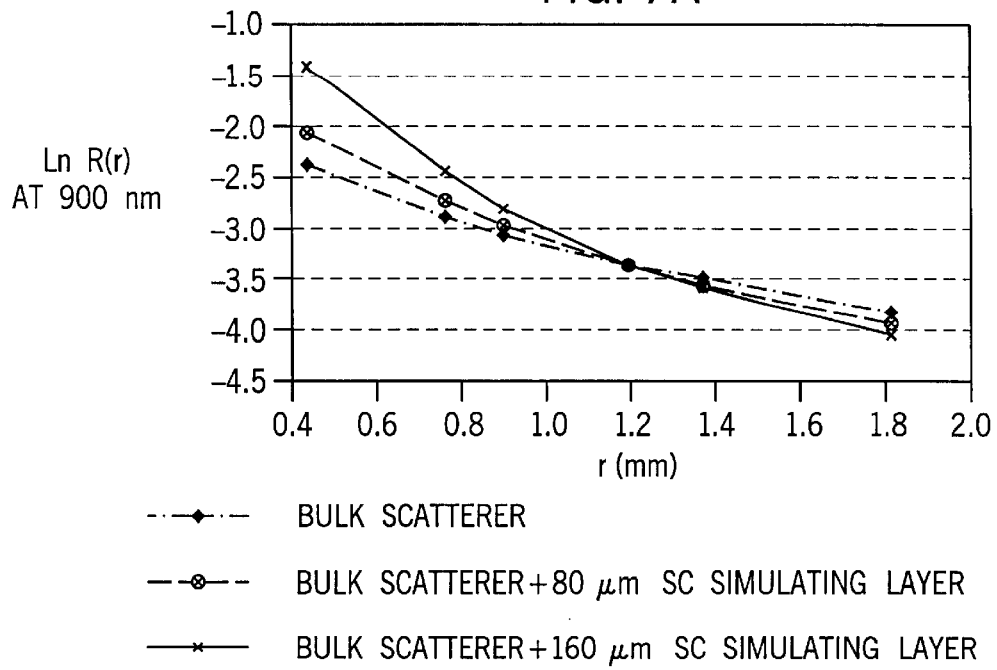
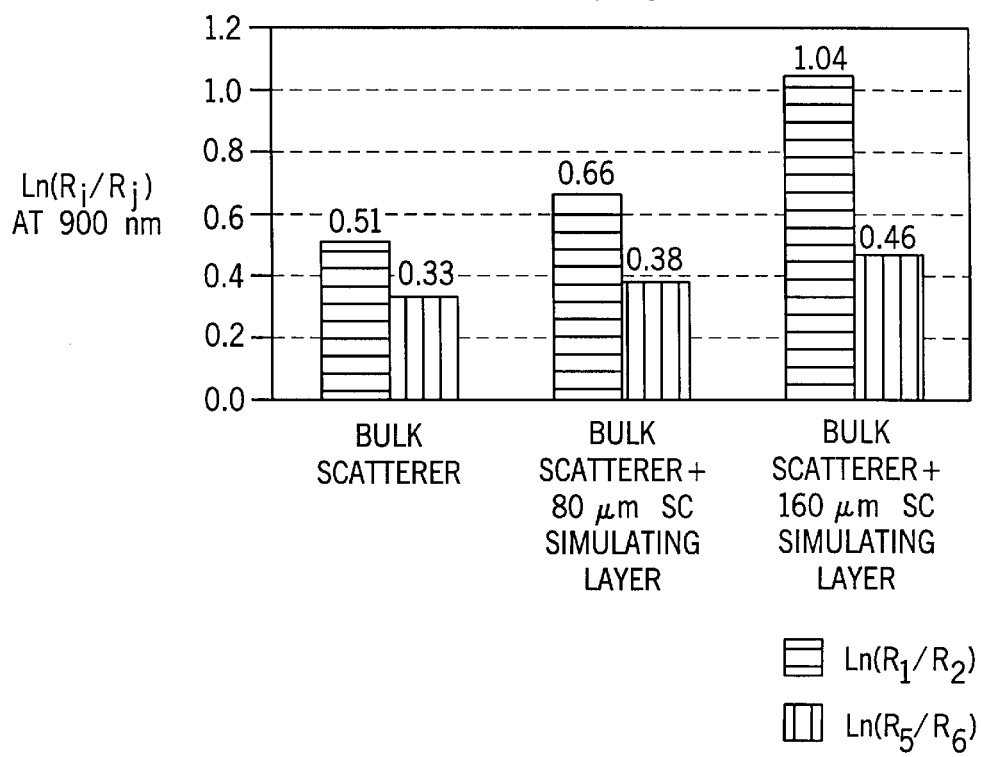

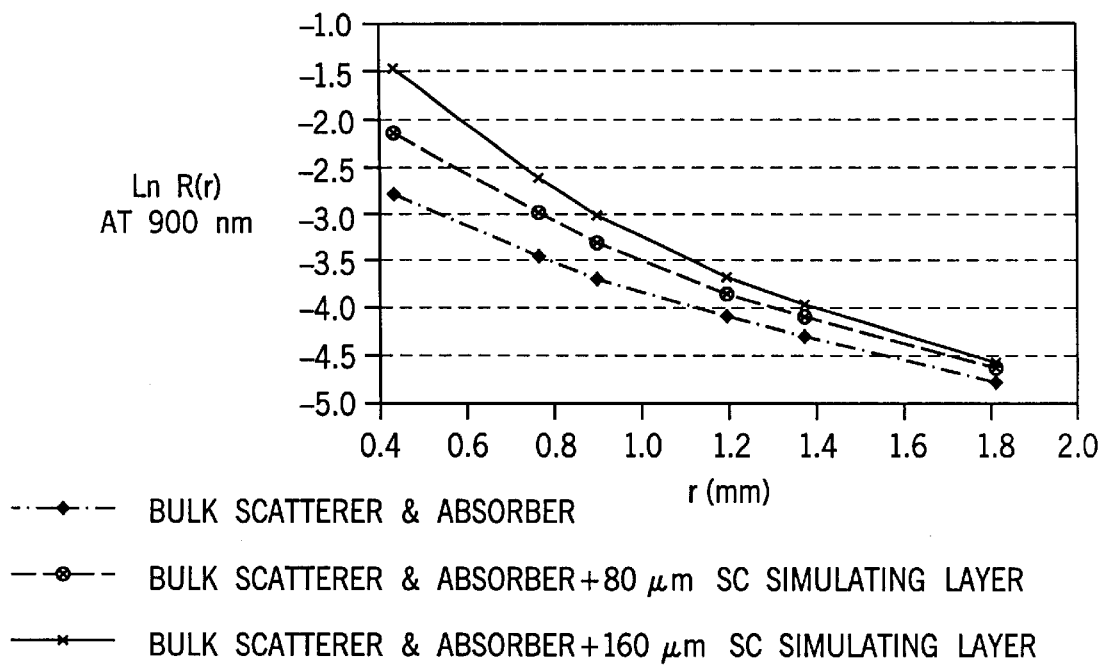
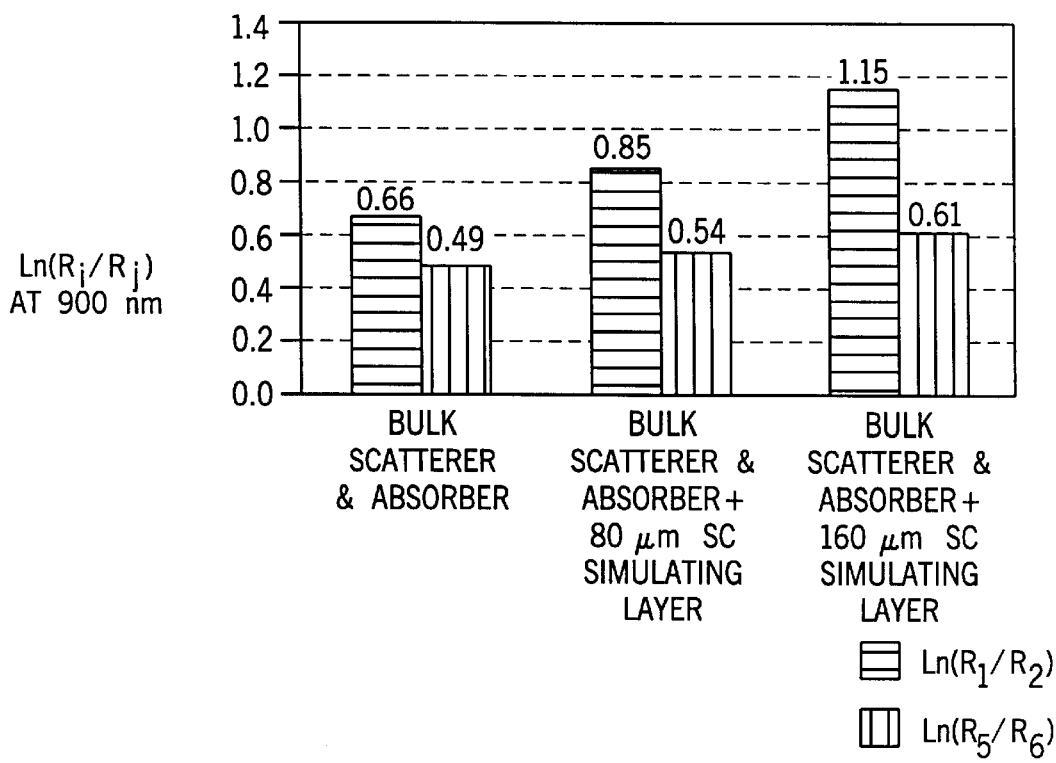

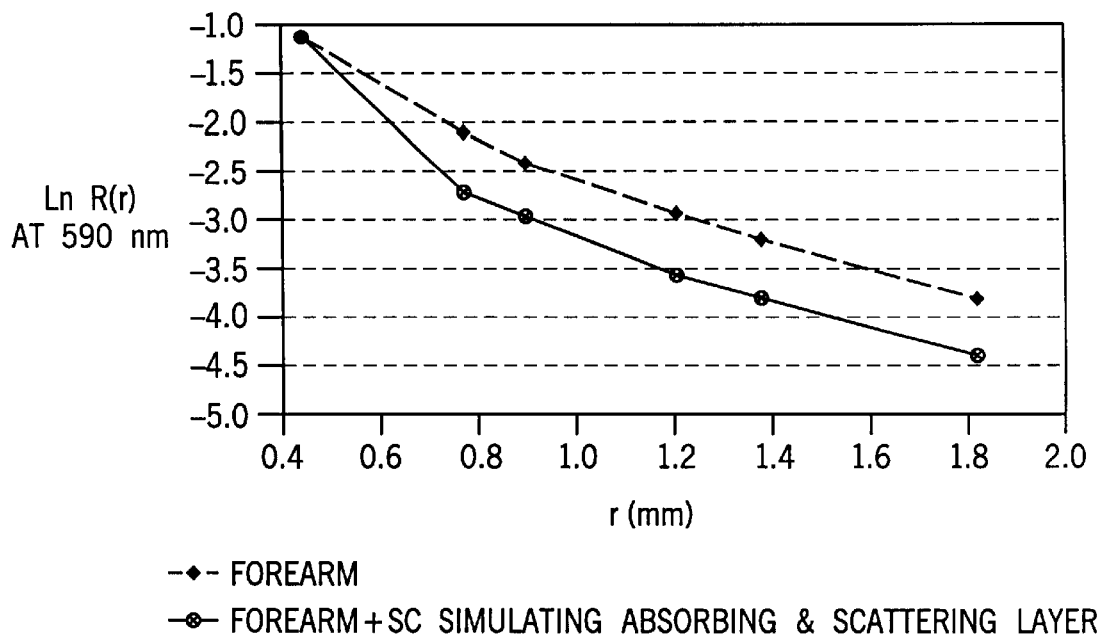
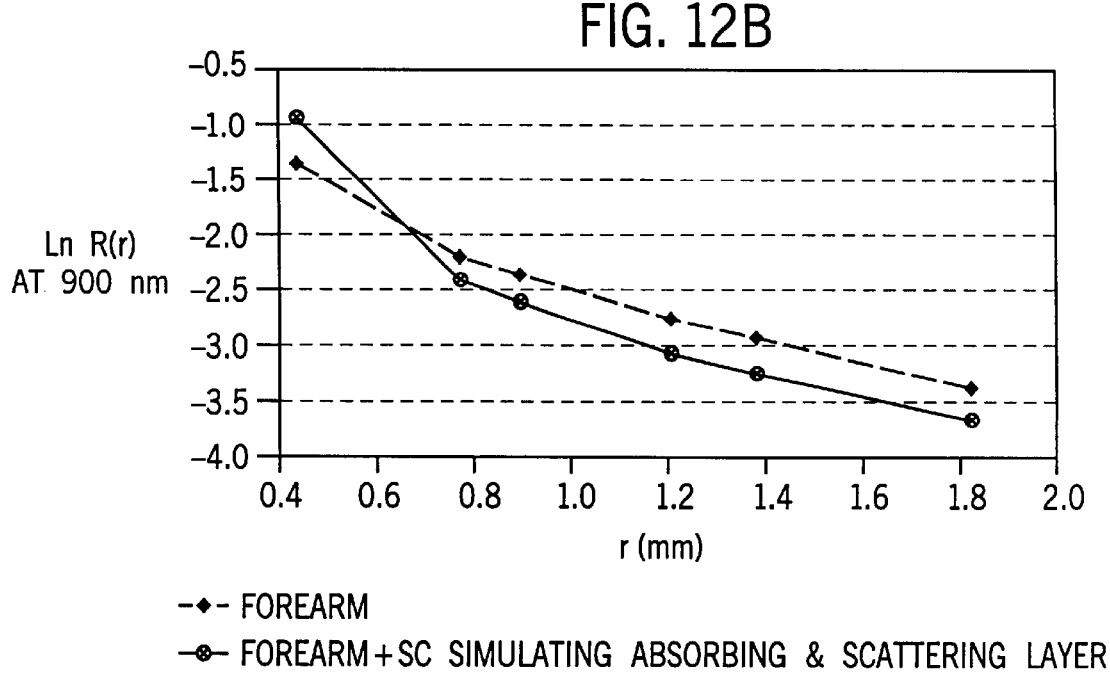

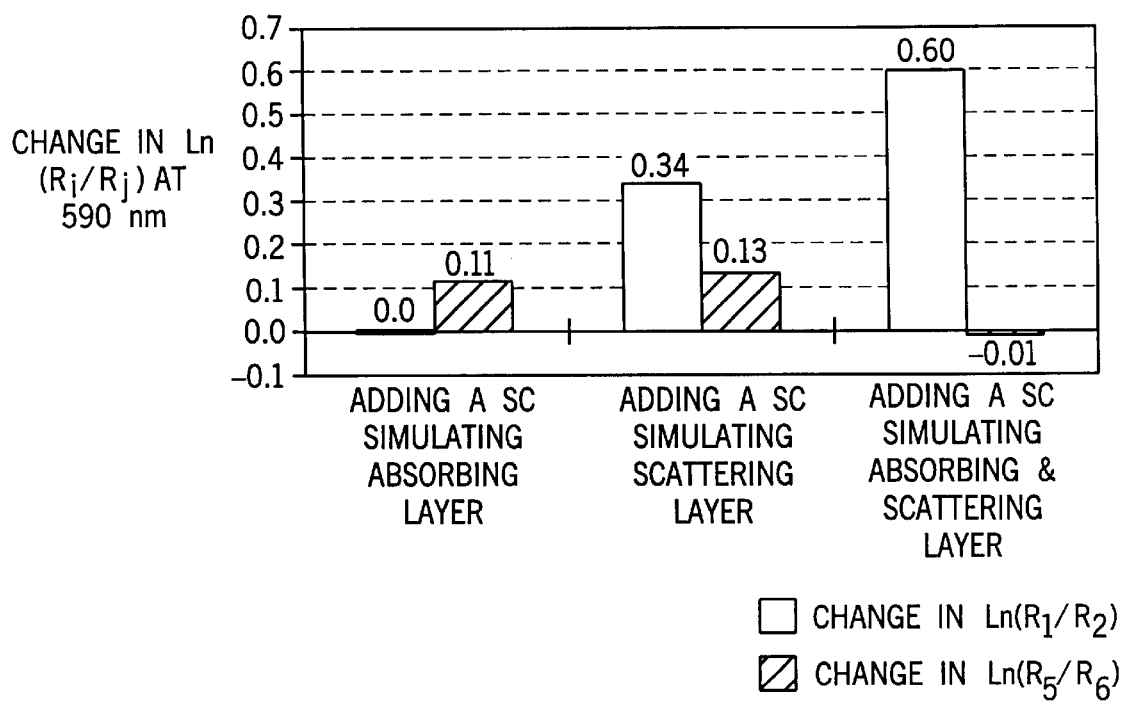
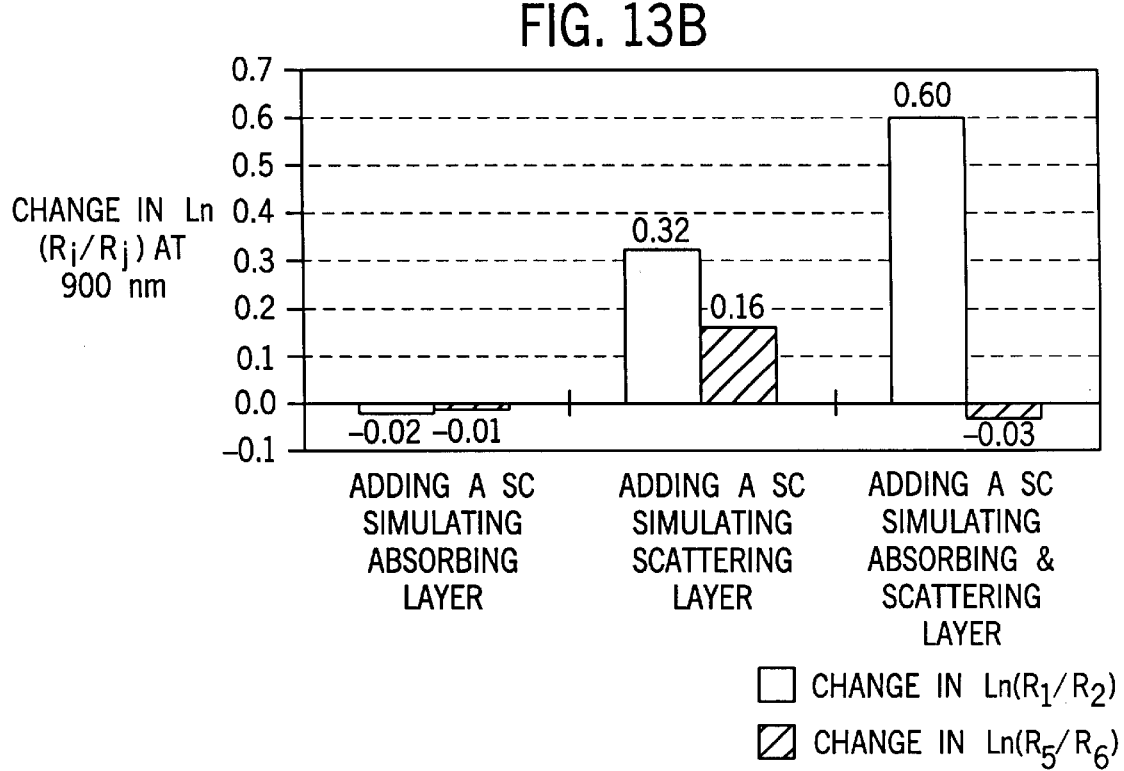

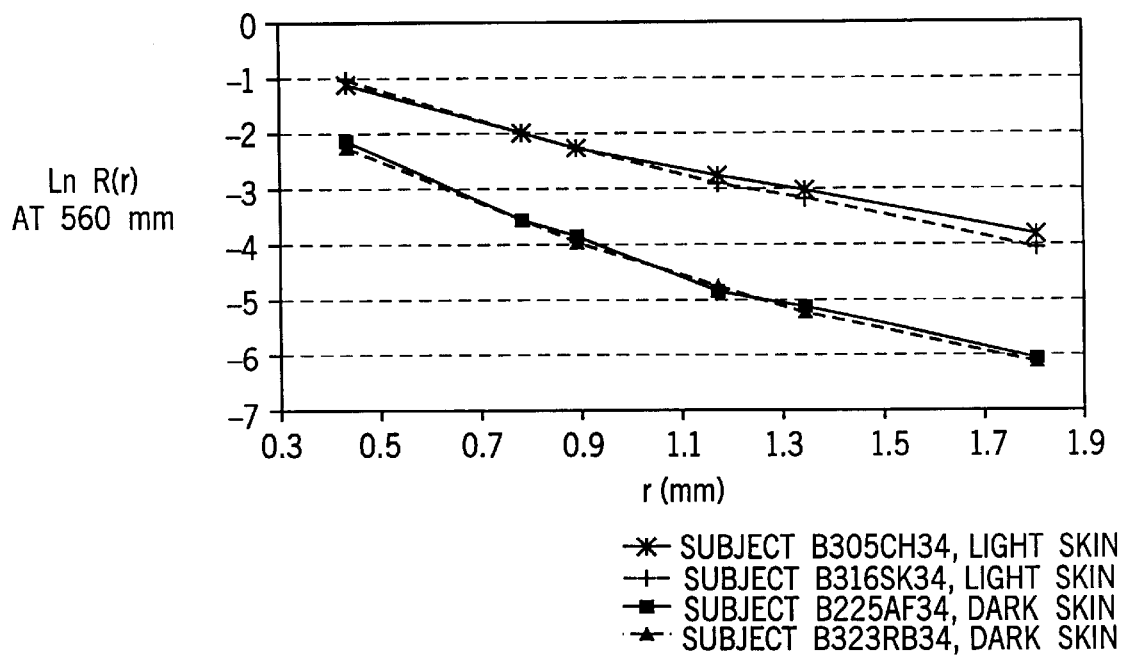
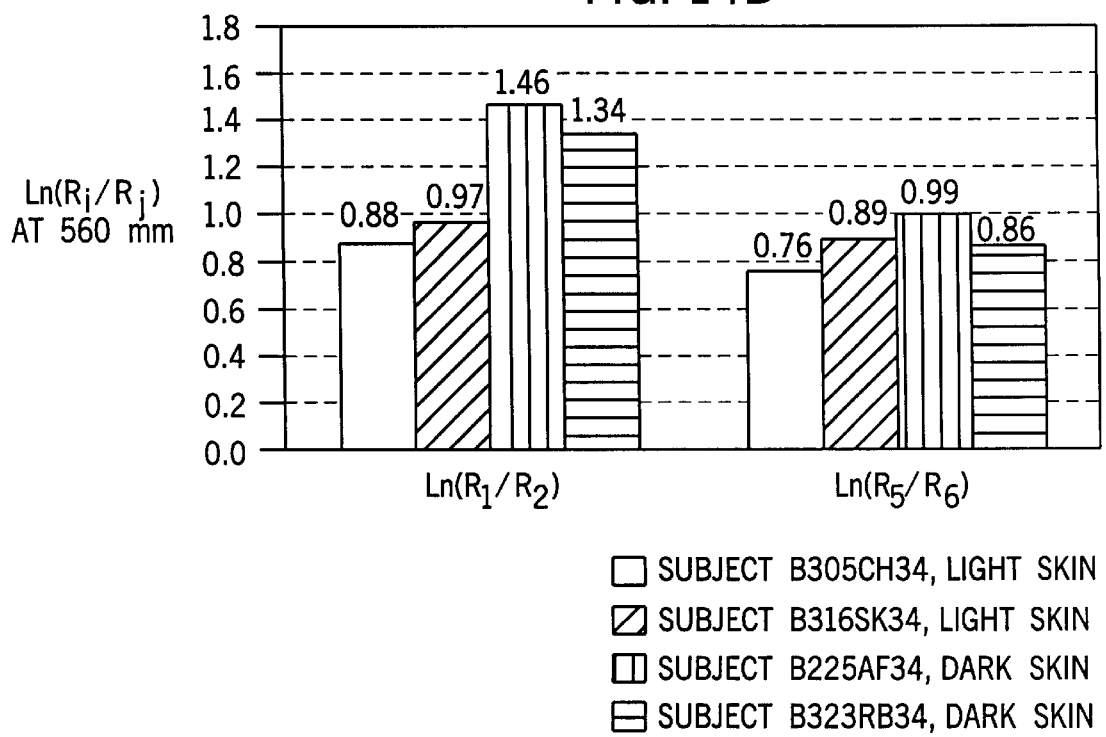

NON-INVASIVE SENSOR CAPABLE OF DETERMINING OPTICAL PARAMETERS IN A SAMPLE HAVING MULTIPLE LAYERS

BACKGROUND OF THE INVENTION

1. Field of the Invention

This invention relates to devices and methods for measuring optical parameters of a sample, e. g., a sample of tissue in a human body. More specifically, this invention relates to devices and methods for the non-invasive determination of one or more optical parameters in vivo in tissues comprising a plurality of layers.

2. Discussion of the Art

Non-invasive monitoring of metabolites by optical devices and methods is an important tool for clinical diagnostics. The ability to determine an analyte, or a disease state, in a human subject without performing an invasive procedure, such as removing a sample of blood or a biopsy specimen, has several advantages. These advantages include ease in performing the test, reduced pain and discomfort to the patient, and decreased exposure to potential biohazards. These advantages will result in increased frequency of testing when necessary, accurate monitoring and control, and improved patient care. Representative examples of non-invasive monitoring techniques include pulse oximetry for oxygen saturation (U.S. Pat. Nos. 3,638,640; 4,223,680; 5,007,423; 5,277,181; 5,297,548). Another example is the use of laser Doppler flowmetry for diagnosis of circulation disorders (Toke et al, "Skin microvascular blood flow control in long duration diabetics with and without complication", Diabetes Research, Vol. 5 (1987), pages 189–192). Other examples of techniques include determination of tissue oxygenation (WO 92/20273), determination of hemoglobin (U.S. Pat. No. 5,720,284) and of hematocrit (U.S. Pat. Nos. 5,553,615; 5,372,136; 5,499,627; WO 93/13706).

Measurements in the near-infrared region of the electromagnetic spectrum have been proposed, or used, in prior art technologies. The 600 nm to 1300 nm region of the electromagnetic spectrum represents a window between the visible hemoglobin and melanin absorption bands and the strong infrared water absorption bands. Light having a wavelength of 600 nm to 1300 nm can penetrate deep enough into the skin to allow use thereof in a spectral measurement or a therapeutic procedure.

Oximetry measurement is very important for critical patient care, especially after the use of anesthesia. Oxygenation measurements of tissue are also important diagnostic tools for measuring oxygen content of the brain of the newborn during and after delivery, for monitoring tissue healing, and in sports medicine.

Non-invasive determination of hemoglobin and hematocrit values in blood would offer a simple, non-biohazardous, painless procedure for use in blood donation centers, thereby increasing the number of donations by offering an alternative to the invasive procedure, which is inaccurate and could lead to the rejection of a number of qualified donors. Non-invasive determination of hemoglobin and hematocrit values would be useful for the diagnosis of anemia in infants and mothers, without the pain associated with blood sampling. Non-invasive determination of hemoglobin has been considered as a method for localizing tumors and diagnosis of hematoma and internal bleeding. Non-invasive determination of hematocrit values can yield important diagnostic information on patients with kidney failure before and during dialysis. There are more than 50 million dialysis procedures performed in the United States and close to 80 million dialysis procedures performed worldwide per year.

The most important potential advantage for non-invasive diagnostics possibly will be for non-invasive diagnosis and monitoring of diabetes. Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (S. L. Robbins, S. L. et al., *Pathologic Basis of Disease,* 3rd Edition, W. B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

The principal treatment for Type I diabetes involves periodic injection of insulin. Appropriate insulin administration can prevent, and even reverse, some of the adverse clinical manifestations of Type I diabetes. Frequent adjustments of the level of glucose in blood can be achieved either by discrete injections of insulin or, in severe cases, by an implanted insulin pump or artificial pancreas. The amount and frequency of insulin administration is determined by frequent or, preferably, continuous testing of the level of glucose in blood (i. e., blood glucose level).

Precise control of blood glucose level in the "normal range", 60 mg/dL to 120 mg/dL, is necessary for Type I and Type II diabetics to avoid or reduce complications resulting from hypoglycemia and hyperglycemia. To achieve this level of control, the American Diabetes Association recommends that diabetics test their blood glucose level five times per day when the control of blood glucose level is necessary. Thus, there is a need for accurate and frequent or, preferably, frequent glucose monitoring to combat the effects of diabetes.

Conventional measurements of blood glucose level in a hospital or a physician's office rely on the withdrawal of a 5 mL to 10 mL blood sample from the patient for analysis. This method is slow and painful and cannot be used for frequent glucose monitoring. An additional problem for hospitals and physicians' offices is the disposal of testing media that are contaminated by blood.

Portable personal glucose meters are the most popular devices for monitoring blood glucose levels. Typically, a drop of blood is obtained by sticking a patient's finger with a sharp object, and the blood obtained is analyzed by means of chemical reactions on a strip. These reactions provide an optical or electrochemical signal. This type of device provides a convenient way to monitor blood glucose level. However, the pain associated with collecting samples of blood, the potential contamination at the puncturing site, the disposal of biohazardous testing materials, the cumbersome procedures, and the chance of making mistakes often prevent patients from using the meters as frequently as recommended by physicians.

Implantable biosensors have also been proposed for glucose measurement. (G. S. Wilson, et al., "Progress toward the development of an implantable sensor for glucose", Clin. Chem., Vol. 38 (1992), pages 1613–1617). These biosensors are electrochemical devices having enzymes immobilized at the surface of an electrochemical transducer. They are usually implanted into a patient's tissue by means of a surgical procedure.

All of the foregoing categories of glucose monitoring techniques have one feature in common: they all involve a procedure whereby the skin of a human body part is disrupted by means of a mechanical device. These techniques are referred to as invasive techniques.

"Non-invasive" (alternatively referred to herein as "NI") glucose-monitoring techniques measure in vivo glucose concentrations without collecting a blood sample. As defined herein, a "non-invasive" technique is one that can be used without removing a sample from, or without inserting any instrumentation into, the tissues. The concept upon which most such technologies are based involves irradiating a vascular region of the body with electromagnetic radiation and measuring the spectral information that results from at least one of four primary processes: reflection, absorption, scattering, and emission. The extent to which each of these processes occurs is dependent upon a variety of factors, including the wavelength and polarization state of the incident radiation and the concentration of analytes in the body part. Concentrations of an analyte, e. g., glucose, are determined from the spectral information by comparing the measured spectra to a calibration curve or by reference to a physical model of the tissue under examination. Various categories of non-invasive measurement techniques will now be described.

NI techniques that utilize the absorption of infrared radiation can be divided into three distinct wavelength regimes: Near-infrared (NIR), mid-infrared (MIR) and far-infrared (FIR). As defined herein, NIR involves the wavelength range from about 600 nm to about 1300 nm, MIR involves the wavelength range from about 1300 nm to about 3000 nm, and FIR involves the wavelength range from about 3000 nm to about 25000 nm. As defined herein, "infrared" (or IR) is taken to mean a range of wavelengths from about 600 nm to about 25000 nm.

U.S. Pat. Nos. 5,086,229; 5,324,979; and 5,237,178 describe non-invasive methods for measuring blood glucose level involving NIR radiation. In general, a blood-containing body part (e. g., a finger) is illuminated by one or more light sources, and one or more detectors detect the light that is transmitted through the body part. A blood glucose level is derived from a comparison to reference spectra for glucose and background interferents.

Due to the highly scattering and absorption nature of the human skin and tissue, light in the 600 nm to 1300 nm spectral range penetrates the skin and underlying tissues to different depths. The penetration depth depends on the wavelength of light and positioning of the source and detector. Analyzing the reflected or transmitted signal without accounting for the effect of different layers of skin can lead to erroneous estimates of the optical properties of the tissue and hence, the concentration of metabolites determined from these measured properties. The stratum corneum, epidermis, dermis, adipose tissue, and muscle layers can all interact with light and contribute to the measured signals. Controlling the penetration depth of the light and understanding the effect of the different layers of the skin on the generated signal are important for the non-invasive determination of metabolites in tissues. This NIR spectral region has been used for determination of blood oxygen saturation, hemoglobin, hematocrit, and tissue fat content. It is also used for exciting and detecting compounds in photodynamic therapy. At longer wavelengths, water absorption bands dominate tissue spectra. There are some narrower spectral windows in the 1500 nm to 1900 nm range and the 2100 nm to 2500 nm range, where both in vitro and in vivo tissue measurements were performed.

Light striking a tissue will undergo absorption and scattering. Most of the scattered photons are elastically scattered, i. e., they have the same frequency as the incident radiation (Rayleigh scattering). A small fraction of the scattered light (less than one in a thousand incident photons) is inelastically scattered (Raman scattering). Unless otherwise indicated herein, "scattering" refers to elastic scattering.

Because of the multiple scattering effect of tissue, optical measurements, whether in transmission or reflectance, will contain tissue scattering information, as well as absorption information. Tissue scattering information includes cell size and cell shape, depth of the tissue layer in which scattering occurs, and refractive index of intracellular fluids and extracellular fluid. Absorption information includes absorption by tissue components, such as hemoglobin, melanin, and bilirubin, and the overtone absorption of water, glucose, lipids, and other metabolites.

Spatially resolved diffuse reflectance (SRDR) techniques are a subset of the elastic scattering methods previously described. In a typical example of a SRDR technique, as shown in FIG. 1A, light is introduced into the surface of a tissue sample, such as a body part, at an introduction site. The diffusely reflected light is measured at two or more detection sites located on the surface of the sample (e. g., the skin) at different distances, r, from the introduction site. The dependence of the intensity of the diffusely reflected light, i. e., reflectance R, as a function of the detection distance (r) is used to derive scattering and absorption coefficients of the tissue sample. These coefficients, in turn, are related to the concentration of analyte(s). Spatially resolved diffuse reflectance techniques have been described by L. Reynolds et al., "Diffuse reflectance from a finite blood medium: application to the modeling of fiber optic catheters", Applied Optics, Vol. 15 (1976), pages 2059–2067. Another use and interpretation were given by R. A. J. Groenhuis et al., "Scattering and absorption of turbid materials determined from reflection measurements. 1: Theory", Applied Optics, Vol. 22 (1983), pages 2456–2462. Yet another application of spatially resolved diffuse reflectance was the determination of compounds in tissue, M. S. Patterson et al., "Quantitative reflectance spectrophotometry for the noninvasive measurement of photosensitizer concentration in tissue during photodynamic therapy", SPIE (Society for Photooptical Instrument Engineering) Proceedings, Vol. 1065 (1989), pages 115–122. Other recent publications include: B. Chance, H. Liu, T. Kitai, Y. Zhang, "Effect of solutes on the optical properties of biological materials", Analytical Biochemistry, Vol. 227 (1995), pages 351–362; H. Liu, B. Beauvoit, M. Kimura, B. Chance, "Effect of solutes on optical properties of biological materials: Models, cells and tissues", Journal of Biomedical Optics, Vol. 1 (1996), pages 200–211; and J. Qu, B. Wilson, "Monte Carlo modeling studies of the effect of physiological factors and other analytes on the determination of glucose concentration in vivo by near infrared optical absorption and scattering measurements", Journal of Biomedical Optics, Vol. 2 (1997), pages 319–325.

Frequency-domain reflectance measurements use optical systems similar to those used for spatially resolved light scattering (reflectance (R) as a function of distance (r)), except that the light source is modulated at a high frequency and a synchronized detector is used (U.S. Pat. Nos. 5,187, 672 and 5,122,974). The difference in phase angle and modulation between the incident beam of light and the reflected beam of light is used to calculate the scattering coefficient and the absorption coefficient of the tissue or scattering medium. U.S. Pat. No. 5,492,769 describes frequency domain method and apparatus for the determination of a change in the concentration of an analyte, and U.S. Pat. No. 5,492,118 describes a method and apparatus for determination of the scattering coefficient of tissues.

Co-pending U.S. application Ser. No. 08/982,839, filed Dec. 2, 1997, assigned to the assignee of this application, describes a multiplex sensor that combines at least two NI measurements in order to compensate for the effects of spectral and physiological variables. Co-pending U.S. application Ser. No. 09/080,470, filed May 18, 1998, assigned to the assignee of this application, describes a non-invasive glucose sensor employing a temperature control. One purpose of controlling the temperature is to minimize the effect of physiological variables.

Although a variety of spectroscopic techniques have been disclosed in the art, there is still no commercially available device that provides non-invasive glucose measurements with an accuracy that is comparable to invasive methods. Signals obtained by prior art methods reflect the analyte information of the tissue as if the tissue comprised a single uniform layer. The signals, however, are vulnerable to the effects of surface layers of the skin, which are significantly different from the deeper layers of the skin in terms of textures, colors, and other properties. Also, prior art methods fail to address the effect of variations in efficiency of optical coupling between the measuring device and the skin. As a result, current approaches to non-invasive metabolite testing, such as glucose monitoring, have not achieved acceptable precision and accuracy.

Thus, there is a continuing need for improved NI instruments and methods that are unaffected by variations in skin structures and layers or account for the effect of skin layers. There is also a need for instruments with simple calibration schemes that can be set in the factory and periodically checked for accuracy in the field.

SUMMARY OF THE INVENTION

This invention involves a method and apparatus for non-invasively measuring at least one parameter of a sample of tissue, such as the absorption coefficient or the scattering coefficient of a layer of skin. Such parameters can be used to determine the concentration of an analyte of interest in the sample of tissue. As will be described more fully below, the present invention measures light that is reflected, scattered, absorbed, or emitted by the sample of tissue from a first pair of average sampling depths, $d_{av1}$, $d_{av2}$ and from at least one other pair of average sampling depths $d_{av3}$, $d_{av4}$, where $d_{av3}$ and $d_{av4}$ are greater than $d_{av2}$ and $d_{av1}$. These average sampling depths are preferably less than 3 mm, more preferably less than 2 mm. Confining the sampling depth in the tissue is achieved by appropriate selection of the distance separating the site at which light is introduced into the sample and the site at which light is collected from the sample after being reflected, scattered, absorbed, or emitted by the sample.

Confining the sampling depth in the tissue provides several advantages. First, confining the sampling depth allows determinations of the optical properties of a specific layer of the sample, e.g., epidermis, and decreases interference from other layers, e. g., stratum corneum, in these determinations. Secondly, the tissue region that is sampled can be more homogeneous than the tissue regions sampled by the devices described in prior art. Thirdly, the signal is obtained from a region of tissue having a substantially uniform temperature. Accordingly, the signal is not likely to be affected by the temperature gradient running from the surface of the tissue into the interior of the tissue.

In the preferred embodiments, this invention involves a method and apparatus for non-invasively measuring at least one parameter of a sample by means of a light introduction site and a plurality of light collection sites, each light collection site comprising a plurality of light collecting elements. The site at which light is introduced into the sample and the sites at which the light reflected, scattered, absorbed, or emitted by the sample is collected for detection occupy a small area on the surface of the tissue. The minimum distance between the site at which light is introduced into the sample and the closest site at which the light is collected is approximately equal to or less than the transport mean free path of a photon in the sample. The transport mean free path is the average distance that a photon can be propagated in a sample without undergoing an absorption event or a scattering event. This minimum distance is on the order of 1 mm for light in the near infrared region of the electromagnetic spectrum in typical samples of tissues. The maximum distance between the site at which light is introduced into the sample and any site at which the light is collected should be less than ten times that of the transport mean free path of a photon in the sample. This maximum distance is on the order of 1 cm for light in the near infrared region of the electromagnetic spectrum in typical samples of tissues. Preferably, the minimum distance between the site at which light is introduced into the sample and the closest site at which the light re-emitted from the sample is collected is less than 0.5 mm, and the maximum distance between the site at which light is introduced into the sample and the furthest site at which the light re-emitted from the sample is collected is less than 6 mm.

In one aspect, this invention involves a method for determining at least one optical parameter of a sample having a plurality of layers, wherein the layers have different properties. The method comprises the steps of:

a) introducing a beam of light into the sample at a light introduction site on a surface of the sample;

b) determining the intensities of light re-emitted from the sample at a plurality of light collection sites on the surface of the sample, at least a first light collection site collecting light re-emitted mainly from a first layer of the sample, at least a second light collection site collecting light re-emitted mainly from a second layer of the sample, the first light collection site being at a first distance from the light introduction site, and the second light collection site being at a second distance from the light introduction site, the first distance being less than said second distance;

c) determining at least one optical parameter of the first layer of the sample; and d) determining at least one optical parameter of the second layer of the sample, the first layer having an average depth, as measured from the surface of the sample, of smaller magnitude than the average depth of the second layer, as measured from the surface of the sample.

In a preferred embodiment of this aspect, the method of this invention for measuring at least one optical parameter of a sample having layers having differing properties comprises the steps of:

a) introducing a beam of light into the sample at a light introduction site;

b) collecting light re-emitted from the sample at a plurality of light collection sites, wherein each of the light collection sites comprises at least two light collecting elements and each of the light collection sites is located at a different distance from the light introduction site;

c) determining the intensity of the light re-emitted at a first light collecting element of a light collection site located at a first distance from the light introduction site and the intensity of the light re-emitted at at least a second light collecting element of the light collection site located at the first distance from the light introduction site;

d) determining the absorption coefficient and the scattering coefficient of the sample at a given depth of the sample by means of a mathematical relationship between intensity of the light re-emitted at the first light collecting element of the light collection site located at the first distance from the light introduction site and intensity of the light re-emitted at at least a second light collecting element of the light collection site located at the first distance from the light introduction site;

e) determining the intensity of the light re-emitted at a first light collecting element of a light collection site located at a second distance from the light introduction site and the intensity of said light re-emitted at at least a second light collecting element of the light collection site located at the second distance from the light introduction site, wherein the second distance is greater than the first distance;

f) determining the absorption coefficient and the scattering coefficient of the sample at a greater depth of the sample than that of step d) by means of a mathematical relationship between intensity of the light re-emitted at the first light collecting element of the light collection site located at the second distance from the light introduction site and intensity of the light re-emitted at at least a second light collecting element of the light collection site located at the second distance from the light introduction site.

Depending upon the number of layers in a sample, the total number of light collection sites may vary. At a minimum, the number of light collection sites should be equal to the number of layers. Also, the separation between a particular light collection site and the light introduction site is determined by the depth and thickness of the particular layer in the sample for which this light collection site is designated. A minimum of two light collecting elements should be included in each light collection site.

In order to provide for the mathematical relationships in steps d) and f), in any light collection site of light collecting elements, the first light collecting element in the light collection site and at least a second light collecting element in the light collection site must be located at different distances from the light introduction site.

One example of the mathematical relation between the light collected at a first light collecting element at a first collection site ($R_1$) and the light collected at at least a second light collecting element at the first collection site ($R_2$) is the logarithm of $1/R_1$ as a function of corresponding logarithm of $R_1/R_2$. The mathematical relationship can be used to determine the absorption and scattering coefficients of the layer of tissue close to the surface of the sample (stratum corneum and epidermis) from the measured reflectance values and a calibration procedure based on known reflectance values.

One possible calibration procedure involves construction of a calibration diagram by plotting the measured values of a function of reflectance at one light collection site distance, e. g., $f(1/R_1)$, versus the measured values of another function of reflectance, e. g., $f(R_1/R_2)$, at that light collection site distance for a series of materials of known measured absorption and scattering coefficients. These materials can be selected from solid plastic disks containing different levels of scattering and absorbing pigments, opaque or translucent glass, liquid suspensions of scattering materials, or the like. From the calibration diagram obtained, one can determine the scattering and absorption coefficients of an unknown sample based on its measured values of $R_1$ and $R_2$. Knowledge of the scattering and absorption coefficients can be used to determine the concentration of an analyte of interest in the layer of tissue close to the surface of the sample. The procedure described above can be repeated for layers of tissue that are located below the layer of tissue close to the surface of the sample. The method of this invention can be applied to any tissue comprising, in effect, two or more layers.

The method of this invention is also applicable for an arrangement wherein a single light collection site and a plurality of light introduction sites are employed. In this variation, the method is also capable of determining at least one optical parameter of a sample having a plurality of layers, wherein each of the layers has different properties. The method comprises the steps of:

a) introducing a plurality of beams of light into a sample at a plurality of light introduction sites on a surface of the sample, a first light introduction site being at a first distance from a light collection site on the surface of the sample, a second light introduction site being at a second distance from the light collection site on the surface of the sample, the first distance being less than the second distance;

b) determining the intensities of light re-emitted from the sample at the light collection site, the light collection site collecting light re-emitted mainly from a first layer of the sample and collecting light re-emitted mainly from a second layer in the sample, the light re-emitted from the first layer being introduced at the first light introduction site, the light re-emitted from the second layer being introduced at the second light introduction site;

c) determining at least one optical parameter of a the first layer of the sample; and d) determining at least one optical parameter of the second layer of the sample, the first layer having an average depth, as measured from the surface of the sample, of smaller magnitude than the average depth of the second layer, as measured from the surface of the sample.

In a preferred embodiment of this variation, the method is also capable of determining at least one optical parameter of a sample having layers having different properties. The method comprises the steps of:

a) introducing beams of light into the sample at a plurality of light introduction sites, wherein each of the light introduction sites comprises at least two illuminating elements, each of the light introduction sites located at a different distance from a light collection site;

b) collecting light re-emitted from the sample at the light collection site;

c) determining the intensity of the re-emitted light resulting from illumination by a first illuminating element of a light introduction site located at a first distance from the light collection site and the intensity of the re-emitted light resulting from illumination by at least a second illuminating element of the light introduction site located at the first distance from the light collection site;

d) determining the absorption coefficient and the scattering coefficient of the sample at a given depth of the sample by means of a mathematical relationship between intensity of the re-emitted light resulting from illumination by the first illuminating element of the light introduction site located at the first distance from the light collection site and intensity of the re-emitted light resulting from illumination by at least a second illuminating element of the light introduction site located at the first distance from the light collection site;

e) determining the intensity of the re-emitted light resulting from illumination by a first illuminating element of a light introduction site located at a second distance from the light collection site and the intensity of the re-emitted light resulting from illumination by at least a second illuminating element of the light introduction site located at a second distance from the light collection site, wherein the second distance is greater than the first distance;

f) determining the absorption coefficient and the scattering coefficient of the sample at a greater depth of the sample than that of step d) by means of a mathematical relationship between intensity of the re-emitted light resulting from illumination by the first illuminating element of the light introduction site located at the second distance from the light collection site and intensity of the re-emitted light resulting from illumination by at least a second illuminating element of the light introduction site located at the second distance from the light collection site.

In order to provide for the mathematical relationships in steps d) and f), in any light introduction site of light illuminating elements, the first illuminating element and at least a second illuminating element must be located at different distances from the light collection site.

Depending upon the number of layers in a sample, the total number of light introduction sites may vary. At a minimum, the number of light introduction sites should be equal to the number of layers. Also, the separation between a particular light introduction site and the light collection site is determined by the depth and thickness of the particular layer in the sample for which this light introduction site is designated. A minimum of two illuminating elements should be included in each light introduction site.

The present invention is particularly advantageous for samples of biological tissue where the presence of multiple layers of tissue, such as skin layers, may affect the result of determination of an optical parameter in a specific layer. Non-invasive measurements may be made on a body part of a patient, e. g., a finger, earlobe, lip, toe, skin fold, or bridge of the nose.

The invention offers several advantages over the prior art. The invention makes it is possible to determine the effect of layers having different optical properties in tissue-simulating phantoms and in human skin.

At small separations between the light introduction site and the light collection site, i. e., where the separation is close to the mean free path of the photon in tissue, the majority of light collected has penetrated the tissue to only a shallow depth. If the separation of the light introduction site from the light collection site ranges over large distances (e. g., 0.5 cm to 7 cm), reflected light collected at the light collection site has been propagated through the stratum corneum, epidermis, dermis, as well as deeper regions of tissue. The light path may also include the subcutis (which has higher fatty adipose tissue content) and underlying muscle structures. These layers provide sources of variability in measurements because of the heterogeneity in cell size, cell packing, blood content, as well as thermal properties.

Better temperature control can be achieved at the shallower depths of penetration in the sampled region. Smaller temperature gradients along the depth of a tissue are encountered when a temperature regulation means is applied (as described in co-pending U.S. application Ser. No. 09/080, 470, filed May 18, 1998, incorporated herein by reference).

Furthermore, for tissue that is heterogeneous along dimensions substantially parallel to the surface of the skin, there is lower probability of photons encountering body components, such as hair, scar tissue, or vein structure, that will cause anomalies in the reflectance measurements. It is also possible to perform measurements on a small localized area of the skin with an optical instrument designed to have the light introduction site close to the light collection site rather than with a light introduction site that is located at a great distance from the light collection site. Thus, it is possible to detect blood vessels and hair fibers and determine their effect on the optical signals.

Optical instruments wherein the light introduction site is separated from the light collection site by a great distance require the use of a large body mass, such as the muscle of the arm, thigh, or the abdomen. Accordingly, the body locations where such an optical instrument can be used are limited, and substantial disrobing and inconvenience for the user are required. Thus, another advantage of the design of the apparatus of the present invention is that optical instruments wherein the distance from the light introduction site to the light collection site is 5 mm or less can be used, particularly with small body parts, such as ear lobes and fingers. However, optical instruments wherein the distance from the light introduction site to the light collection site is 5 mm or less can also be used with larger body parts, such as the forearm, thigh, or abdomen.

Another advantage of a small distance between light introduction site and the light collection site is the higher signal to noise ratio obtainable at small separations, due to increases in the amount of light ultimately reaching the detector. Thus simpler, inexpensive, rugged components, such as light emitting diodes, small flash lamps, and incandescent lamps, can be used as sources of light, and inexpensive commercially available photodiodes can be used as detectors. Optical instruments having a large separation between the light introduction site and the light collection site require laser diodes as source of light and photomultiplier tubes as detector, because weaker signals are generated.

BRIEF DESCRIPTION OF THE DRAWINGS

FIG. 6A is a graph illustrating the spatially resolved diffuse reflectance signal at 590 nm of a bulk scattering medium (a suspension comprising a lipids emulsion) with and without layers simulating the stratum corneum.

FIG. 6B is a graph illustrating the sensitivity of the slope of the spatially resolved diffuse reflectance signal at 590 nm at different separations of the light introduction site from the light collection site to changes in the optical properties of a layer that simulates the stratum corneum.

FIG. 7A is a graph illustrating the spatially resolved diffuse reflectance signal at 900 nm of a bulk scattering medium (a suspension comprising a lipids emulsion) with and without layers simulating the stratum corneum.

FIG. 7B is a graph illustrating the sensitivity of the slope of the 900 nm spatially resolved diffuse reflectance signal at different separations of the light introduction site from the light collection site to changes in the optical properties of a layer that simulates the stratum corneum.

FIG. 9A is a graph illustrating the spatially resolved diffuse reflectance signal at 900 nm of a bulk scattering medium (a suspension comprising a lipids emulsion with a blue dye added) with and without a layer simulating the stratum corneum.

FIG. 9B is a graph illustrating the sensitivity of the slope of the 900 nm spatially resolved diffuse reflectance signal at different separations of the light introduction site from the light collection site to changes in the optical properties of a layer simulating the stratum corneum.

FIG. 12A is a graph illustrating the spatially resolved diffuse reflectance signal at 590 nm of a Caucasian volunteer with and without a layer simulating the stratum corneum, the layer having both absorbing and scattering properties.

FIG. 12B is a graph illustrating the spatially resolved diffuse reflectance signal at 900 nm of a Caucasian volunteer with and without a layer simulating the stratum corneum, the layer having both absorbing and scattering properties.

FIG. 13A is a graph illustrating the sensitivity of the slope of the spatially resolved diffuse reflectance signal at 590 nm, at different separations of the light introduction site from the light collection site, to changes in the optical properties of a layer simulating the stratum corneum.

FIG. 13B is a graph illustrating the sensitivity of the slope of the spatially resolved diffuse reflectance signal at 900 nm, at different separations of the light introduction site from the light collection site, to changes in the optical properties of a layer simulating the stratum corneum.

FIG. 14A is a graph illustrating the spatially resolved diffuse reflectance signal at 590 nm of the left arms of Caucasian (light-skinned) and African-American (dark-skinned) volunteers.

FIG. 14B is a graph illustrating the sensitivity of the slope of the spatially resolved diffuse reflectance signal at 590 nm, at different separations of the light introduction site from the light collection site, to changes in the melanosome content of the top skin layers of the left arms of Caucasian (light-skinned) and African-American (dark-skinned) volunteers.

DETAILED DESCRIPTION

Figure 1A:
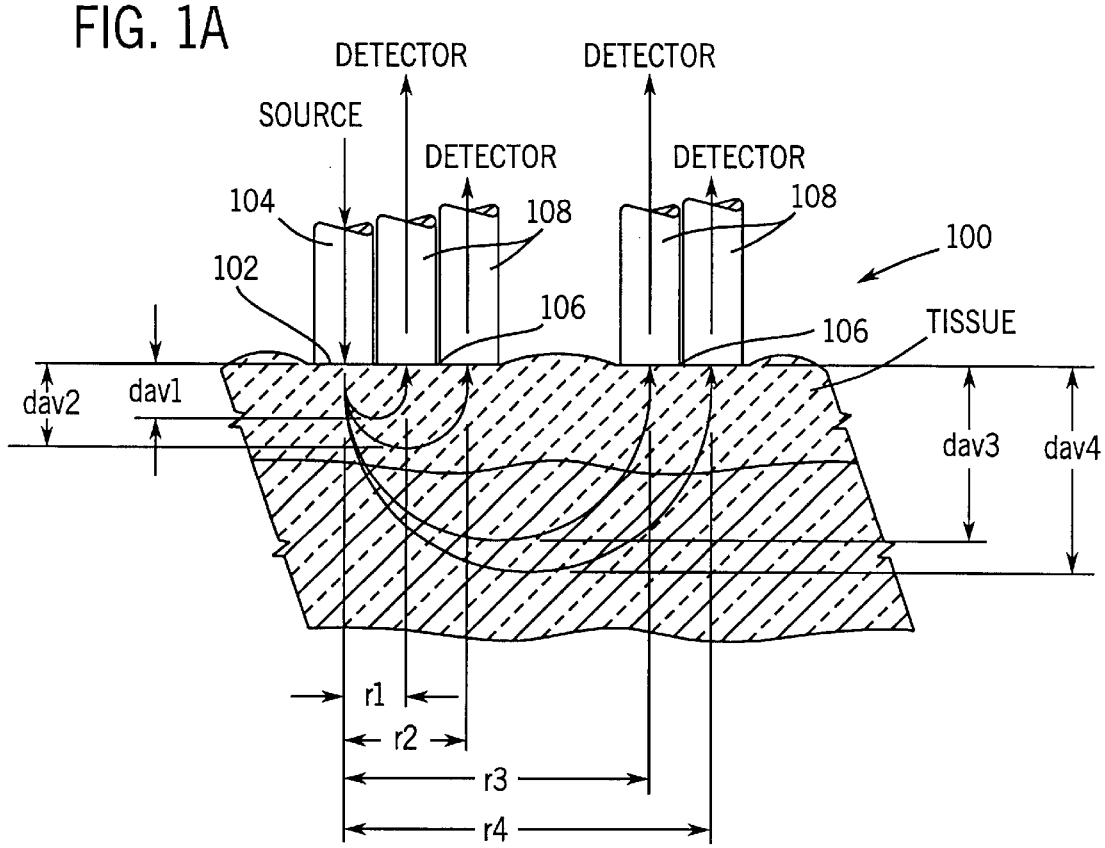
FIGS. 1A and 1B are a schematic diagrams illustrating (1) an arrangement of light collecting elements with respect to the light introduction site and (2) the average sampling depth, $d_{av}$, for a given separation of light collections site from the light introduction site.

As used herein, the expression "optical properties" refers to the absorption, scattering, emission, and depolarization properties of the tissues. The expression "optical parameter" refers to a parameter that describes and defines an optical property of a medium and its components. Examples of optical parameters include absorption coefficients, scattering coefficients, anisotropy factors, transport optical mean free path, extinction coefficients of analytes. The expression "scattering medium" refers to a medium that both scatters light and absorbs light. The expression "absorption coefficient " (i. e., $\mu_a$) refers to the probability of light absorption per unit path length. The expression "scattering coefficient " (i. e., $\mu_s$) refers to the probability of light scattering per unit path length. The expression "anisotropy factor" (i. e., g) refers to the average cosine of the scattering angle for a multiply scattered photon. The expression "reduced scattering coefficient " (i. e., $\mu_s'$) refers to the probability of equivalently isotropic (uniform in all directions) scattering per unit path length. The reduced scattering coefficient is related to the scattering coefficient $\mu_s$ and the anisotropy factor g by the relationship $\mu_s'=(1-g)\mu_s$. The expression "transport photon mean free path " (i. e., $1/(\mu_a+\mu_s')$ refers to the mean path length for a photon traveling in a medium between two consecutive photon-medium interactions. Photon-medium interactions include (1) a scattering event followed by a scattering event and (2) a scattering event followed by an absorption event. The expression "effective scattering coefficient" refers to the transport attenuation coefficient, $\mu_{eff}=\sqrt{3\mu_a(\mu_a+\mu_s')}$. The expression "penetration depth " (i. e., $\delta$) means the reciprocal of the effective attenuation coefficient, $\delta=1/\mu_{eff}$. Penetration depth is related to to the change of light intensity in a scattering medium as a function of distance traveled by the light along the same path as the incident light. The expression "Monte Carlo simulation" refers to a statistical method that can be used to trace photon propagation in a scattering medium by means of numerical simulation. The expression "diffuse reflectance" means a measure of the intensity of light that is re-emitted from the surface of a sample in all directions except the direct reflection direction when the surface is illuminated by incident light. The expression "spatially resolved diffuse reflectance" refers to a measurement of light that is re-emitted from a sample and collected at several light collection sites and at a defined distance from a light introduction site. Alternatively, this expression can refer to the light collected at a given light collection site on the sample boundary as a result of introducing light at discrete light introduction sites located on the same boundary at defined distances from the light collection site. The expression "frequency domain measurement" refers to a measurement of light involving the phase angle and/or the amplitude change of modulated incident light, at a given separation distance of a light introduction site from a light collection site, as the light transverses a scattering medium. The expression "beam of light" means a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber. The expression "light introduction site" means a location on the surface of a sample, e. g., a body part, tissue, or the like, at which light is injected or inserted into the sample. The source of the light can be located at the light introduction site or can be located remote from the light introduction site. If the source of light is located remote from the light introduction site, the light must be transmitted to the light introduction site by light transmitting means, such as, for example, optical fibers. The expression "illuminating element" means a component located at the light introduction site that delivers light to the sample, e. g., a body part, tissue, or the like. The illuminating element is typically an optical fiber that transmits light from a source of light to the light introduction site. However, if the source of light can be located at the light introduction site, the source of light can be the illuminating element. The expression "light collection site" means a location on the surface of a sample, e. g., a body part, tissue, or the like, at which light that is re-emitted from the sample is accumulated. The detector, which determines the intensity of the re-emitted light, can be located at the light collection site or can be located remote from the light collection site. If the detector is located remote from the light collection site, the light must be transmitted to the detector by light transmitting means, such as, for example, optical fibers. The expression "light collecting element" means a component covering an area at the light collection site that accumulates light that is re-emitted from the sample, e. g., a body part, tissue, or the like. The light collecting element is typically an optical fiber that transmits light from the light collection site to a detector. However, if the detector can be located at the light collection site, the detector can be the light collecting element. The term "sample" means a biological or non-biological material that scatters and absorbs light. Samples include, but are not limited to, tissue, blood, urine, and other biological solids and fluids. Samples can be homogeneous or heterogeneous and can consist of a single layer or a plurality of layers. As used herein, the term "tissue" includes tissue of any animal, including humans. Moreover, the term "tissue" is intended to include the intact tissue of a living animal, including humans. The term "distance" means (1) the distance as measured from the center of one site to the center of the other site when referring to the distance between two sites; (2) the distance from the center of one element to the center of the other element when referring to the distance between two elements; (3) the distance between the center of a given site and the center of an element not in that site when referring to the distance between a given site and an element not in that site. The expression "re-emitted light" means a group of photons emerging from a sample as a result of the scattering, reflection, absorption, and emission of the light that illuminates the sample. As used herein, the term "light" means electromagnetic radiation. Preferably, the light has a wavelength ranging from about 400 nm to about 10,000 nm, more preferably from about 400 nm to about 2500 nm, most preferably from about 500 to about 1500 nm.

The effect of samples and media, particularly sample of tissue, on light will now be discussed briefly. For samples and media that slightly scatter light, Beer's law describes the light fluence within a sample as follows:

$$I = I_o \exp(-\mu_t z) \tag{1}$$

where

I represents the light fluence at a distance, z, into the sample, $I_o$ represents the intensity of incident light, and $\mu_t$ represents a total attenuation coefficient.

$\mu_t$ is the sum of the absorption coefficient, $\mu_a$, and the reduced scattering coefficient, $\mu_s'$. The mean free path of a photon describes the average distance traveled by a photon either (1) between a first scattering event followed by a second scattering event or (2) between a scattering event followed by an absorption event, and is defined as $1/\mu_t$.

At wavelengths of visible and NIR light, scattering dominates absorption in biological tissues (i. e., $\mu_s \gg \mu_a$) and photon propagation deviates significantly from Beer's law. Tissue scattering occurs because of a mismatch between the indices of refraction of either the extracellular fluid (ECF) or the intracellular fluid (ICF) and the cellular membranes of the tissue. As used herein, the expression "cellular membranes" encompasses both the cell membrane as well as the membranes of organelles, such as mitochondria or collagen fibrils. Besides undergoing scattering and absorption, photons can be reflected at the interface between tissue and an illuminating element; photons can also be re-emitted out of the tissue.

A practical approach for describing the transfer of light energy through a scattering medium uses radiative transport theory. In the radiative transport formalism, light propagation is considered equivalent to the flow of discrete photons, which may be locally absorbed by the medium or scattered by the medium. For samples and media that highly scatter light, where the distance from the light introduction site to the light collection site is much larger than the transport photon mean free path, the radiative transport theory can be simplified to yield the Diffusion Theory approximation. The Diffusion Theory describes photon propagation in tissues by the absorption coefficient, $\mu_a$, and the reduced scattering coefficient $\mu_s' = \mu_s[1-g]$, where the anisotropy factor, g, represents the average cosine of the angle at which a photon is scattered. Typical values of g for tissues are $0.9 < g < 1.0$ (forward scattering). The attenuation of photons in tissues is described by an effective attenuation coefficient, $\mu_{eff}$, as follows:

$$\mu_{eff} = \sqrt{(3\mu_a(\mu_a + \mu_s'))} = \sqrt{(3\mu_a[\mu_a + \mu_s(1-g)])} \tag{2}$$

The value of $\mu_{eff}$ can be calculated from scattering measurements (such as by spatially resolved diffuse reflectance techniques) and both $\mu_a$ and $\mu_s'$ can be derived from measurements of $\mu_{eff}$ under different conditions. In turn, changes in the values of $\mu_a$ and $\mu_s'$ can be related to tissue parameters, such as the concentration of an analyte.

Light fluence within the sample, where light may undergo frequent scattering events, is described by the following formula:

$$I = I_o \exp(-\mu_{\mathit{eff}} z) \quad (3)$$

where I, $I_o$, and z are defined as above and $\mu_{\mathit{eff}}$ is defined as above and differs from the $\mu_t$ defined in Equation (1).

For tissue samples irradiated at visible and near-infrared wavelengths of light, the size of the scattering material in the tissue is near the wavelength of light, and the reduced scattering coefficient, $\mu_s'$, can be expressed using Mie theory as follows:

$$\mu_s' = \mu_s(1-g) = 3.28\pi a^2 \rho (2\pi a n_{ex}/\lambda)^{0.37} (m-1)^{2.09} \quad (4)$$

where

ρ represents the volume density, i. e., number of particles per unit volume, a represents the radius of the scattering particle (e. g., cells, mitochondria, or collagen fibrils), $n_{ex}$ represents the refractive index of the medium (ECF or ICF), $m = (n_{in}/n_{ex})$, the ratio of the refractive index of the scattering particle $n_{in}$ to the refractive index of the medium $n_{ex}$, and λ represents the wavelength of the light.

See R. Graaff, et al., "Reduced light-scattering properties for mixtures of spherical particles: a simple approximation derived from Mie calculations", Applied Optics, Vol. 31 (1992), pages 1370–1376.

For a given wavelength of incident light, $\mu_s'$ changes directly with either the size of the scattering particle, "a", or the refractive index ratio "m", as shown in Equation (4). Because the refractive index of the scattering particles, $n_{in}$, remains relatively constant, $\mu_s'$ is influenced mostly by $n_{ex}$ and particle radius "a". For example, an increase in concentration of glucose, or concentration of other solute, reduces tissue scattering by decreasing the difference in refractive index between the ICF/ECF and the cellular membranes. Variations in $n_{ex}$ are not specific for a particular analyte, however, and are affected by any change in the total concentration of solutes in the ECF, including salts and proteins. The values of $n_{ex}$ is also susceptible to changes in physiological variables, such as temperature of the tissue.

Determination of $\mu_a$, $\mu_s$, and g of a tissue at different wavelengths can give information on physical and chemical properties of the tissue, such as concentration of analytes, cell sizes, and tissue heterogeneity. Methods of determining $\mu_{\mathit{eff}}$, $\mu_s'$, and $\mu_a$ are known in the art. One of these methods is the measurement of diffuse reflectance of the skin tissue. In a diffuse reflectance measurement, the measured reflectance is a function of the reduced scattering coefficient $\mu_s'$, the absorption coefficient $\mu_a$, the refractive index of the scattering medium $n_s$, and the refractive index of the surrounding layer $n_o$, which is usually air.

Another method of measuring the absorption and scattering coefficients is referred to as spatially resolved diffuse reflectance, wherein the value of reflectance is a function of the distance of the light introduction site from the light collection site. In this method, the intensity of the light re-emitted from a sample is measured at several distances from the site at which light is introduced into the sample. Under certain conditions, intensity of the re-emitted light is related to the separation of the light introduction site from the light collection site by the relationship:

$$R(r) = K_o [\exp(-\mu_{\mathit{eff}} r)]/r \quad (5)$$

or $$Ln[r \cdot R(r)] = Ln(K_o) - \mu_{\mathit{eff}} r \quad (6)$$

where R(r) represents the intensity of light re-emitted from a sample at a light collection site, which is separated from the light introduction site by a distance r, and $K_o$ is a constant.

For a given measurement, the logarithm of the product of the intensity of the re-emitted light as a function of distance, R(r), times the separation distance between the light introduction site and the light collection site, r, may be plotted against the separation distance r. The plot is linear at large separations of the light introduction site from the light collection site. This linear region is known as the diffusion theory limit. Under these conditions the absolute value of the slope of the line is the effective attenuation coefficient $\mu_{\mathit{eff}}$. Other methods for determination of optical properties of tissues are described in the art. These methods include collimated transmittance and frequency domain measurements.

For the spatially resolved diffuse reflectance measurement that is outside the diffusion theory limit, an effective way of establishing the relationship between R(r) and $\mu_a$ and $\mu_s'$ is the Monte Carlo simulation. This numerical iteration algorithm requires the fewest assumptions in comparison with other scattering theories.

The present invention involves methods and instruments for the measurement of optical properties of tissues taken across a skin boundary, while accounting for the effects of skin layers on the properties measured. The measurement of optical properties of tissue across a skin boundary is adversely affected by the non-homogeneity of the different layers of the skin. Prior art methods and devices ignore the effect of multiple layers of skin tissue on the measured optical properties. Thus, U.S. Pat. Nos. 5,057,695; 5,551,422; 5,676,143; 5,492,118; 5,419,321; 5,632,273; and 5,513,642 are silent as to the effect of different layers of skin on optical measurements, and they disclose no methods or instruments that address this issue. Other prior art methods use widely separated sources of light and detectors of light and a diffusion theory approach to map deep tissue layers. These devices operate on large body masses such as the skull, thigh, or large arm muscles. Studies on blood circulation in skin show that cutaneous microcirculation occurs at depths of 1 to 2 mm below the skin's epidermal surface (I. M. Braverman, "The Cutaneous microcirculation: ultrastructure and microanatomical organization", Microcirculation, Vol. 4 (1997), pages 329–340). Thus, measurement of optical properties close to the surface of the skin can provide useful information on the effect of blood circulation on the concentration of metabolites in tissues that are close to the surface of the skin. Also, studies of blood circulation close to the surface of the skin by means of laser Doppler flowmetry have shown that laser Doppler flowmetry is a good tool for diagnosing peripheral circulatory disease.

Figure 1B:
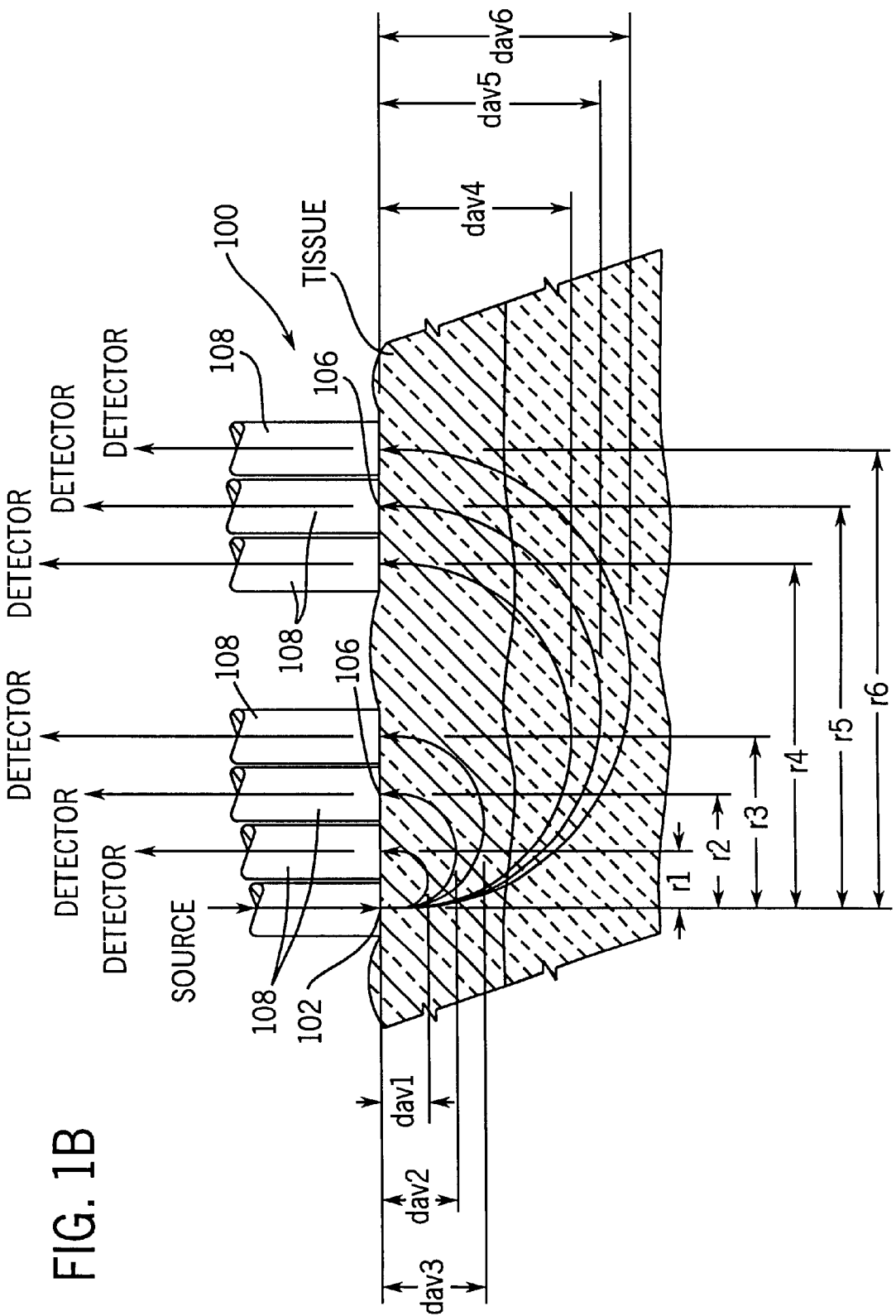

As shown in FIGS. 1A and FIG. 1B, the apparatus 100 of this invention comprises a means for introducing light into tissue through a defined light introduction site 102. The light is introduced by means of an illuminating element 104. At small distances from the light introduction site 102 are located a plurality of light collection sites 106 comprising light collecting elements 108, which collect the light re-emitted from tissue for measurement of the intensity of the re-emitted light at one or more detectors (not shown). The source of light (not shown) for providing light at the light introduction site 102 can be a focused beam of light, a collimated beam of light, or a surface-mounted light emitting diode or a laser diode in contact with the skin. Other sources of light can also be used. In addition, the source of light can be remote from the light introduction site 102, in which case a fiber tip can be used to carry light from the remote source of light. Re-emitted light is collected at several sites located at different distances from the light introduction site 102 and directed towards one or more detectors that measure the intensity of the collected light. Re-emitted light can be collected by any of several means. Representative examples of these means of collecting re-emitted light include, but are not limited to, fibers that are in contact with the skin and a mask with holes at predetermined distances from the light introduction site. The light thus collected can be imaged into a charge coupled device (CCD) camera, a series of photodiodes in contact with the skin or a one-dimensional or a two-dimensional photodiode array, or any other suitable type of detector.

Although the previous discussion has focused primarily upon a single light introduction site and a plurality of light collection sites comprising light collecting elements, in an alternative embodiment, a plurality of light introduction sites and a single light collection site can be used. A single light collection site replaces the light introduction site, and the light collection sites at distances $r_1$ through $r_n$ are replaced by a plurality of light introduction sites. See FIGS. 1A and 1B for examples of distances $r_1$ through $r_n$.

The apparatus of the present invention requires that the sites for introducing light and for collecting light be closely spaced. Thus, the maximum distance between the light introduction site and any light collection site is less than 10 mm, preferably less than 6 mm, more preferably less than 4 mm. The minimum distance between the sites for introducing light and for collecting light must be less than the mean free path of a photon in the medium. The mean free path of a photon is defined as $1/(\mu_a+\mu_s')$. For a typical tissue illuminated with light at a wavelength of 600 nm to 900 nm, the mean free path of a photon ranges from about 0.6 mm to about 1.2 mm. The penetration depth in the tissue ranges from about 0.7 mm to about 2 mm. Thus, the smallest separation between the light introduction site and the site at which re-emitted light is collected should be less than 600 micrometers, preferably from about 200 micrometers to about 400 micrometers. These distances are in contrast with those disclosed in an article by Kumar et al. Kumar et al. recommend that the separation between the light introduction site and the light collection site be greater than 4 mm, in order to avoid the structural effects of the surface of the skin. See G. Kumar, J. M. Schmitt, "Optical probe geometry for near-infrared spectroscopy of biological tissue", Applied Optics, Vol. 36 (1997), pages 2286–2293.

Another feature of the preferred embodiment of this invention is that there are two or more light collecting elements at each light collection site in the case of a single light introduction site. Similarly, there are two or more light introducing elements at each light introduction site in the case of a single light collection site. Although the embodiment in which a plurality of light collection sites comprising a plurality of light collecting elements will now be discussed, the distance relationships between elements also apply to the embodiment in which a plurality of light introduction sites comprise a plurality of illuminating elements. The light collecting elements at each light collection site are very close to each other. The light collecting elements at each light collection site are arranged to cover distances that are either in very close proximity to the light introduction site, near the light introduction site, or greatly separated from the light introduction site. FIGS. 1A and 1B show a schematic arrangement of a light introduction site and light collection sites. The light collecting elements, which can be optical fibers, are preferably adjacent to each other, i. e., almost touching each other, or are separated by a very small distance, which is typically less than the linear dimension of the cross section of a light collecting element. Light collecting elements can be also arranged in groupings of three or more. Light collecting elements at a given light collection site are very close to each other and well separated from light collecting elements at other light collection sites.

The light collecting elements can be arranged in a structure, such as a non-reflective plastic housing or a non-reflective metal housing to decrease the probability of scattered light re-entering the surface of the skin. Alternatively, a set of optical fibers mounted in a transparent plastic holder can be used to divert the re-emitted light away from the skin. Light collecting elements can be arranged in holes drilled in the housing. A preferred structure for an optical instrument of this invention involves arranging optical fibers in a hexagonal close-packed fiber bundle. Some of the fibers are used for illumination and others are used for collection of light. Other fibers can be used to divert scattered light away from the surface of the skin into a light trap, such as a non-reflective hollow cone, to prevent its re-introduction into the surface of the tissue.

The diffusely reflected light is measured, at each wavelength, as a function of the distance between the light introduction site and the light collection site. The signal is amplified and is corrected for fluctuation of the light source and variation of the fiber throughput. The corrected signal is used for calculating the absorption coefficient and the scattering coefficient of the sample.

Absorption and scattering coefficients can be determined from the output of the apparatus of this invention, Monte Carlo modeling, and a calibration procedure. Calibration can be carried out by determining the spatially resolved diffuse reflectance values of a set of materials of known optical properties. These materials are known as tissue-simulating phantoms. They include lipid suspensions, such as Intralipid® (Pharmacia, Clayton, N.C.) and Liposyn® (Abbott Laboratories, North Chicago, Ill.). The lipid suspension is diluted to generate suspensions having known values of scattering coefficients. A colored compound, hemoglobin, or blood is added to the suspension to generate different values of absorption coefficients. Alternatively, plastic rods or sheets containing colored pigments can be used. Also, polished pieces of scattering glass, such as opal glass, can be used to generate reference values for absorption and scattering coefficients. Absorption coefficients and scattering coefficients of these phantoms are usually determined by independent standard optical methods.

An experimental calibration diagram can be established by measuring spatially resolved diffuse reflectance values $R(r_1), R(r_2), R(r_3), \ldots, R(r_n)$ of a series of phantoms having known values of $\mu_a$ and $\mu_s'$. After the spatially resolved diffuse reflectance values are obtained, one can plot one function of the magnitude of the measured reflectance values on one axis (the Y axis) versus the corresponding slope of the measured reflectance values ($\partial R/\partial r$) on the X-axis for each pair of the absorption and scattering coefficients of the tissue-simulating phantoms. A set of scattering coefficient curves is obtained by connecting adjacent points in the plot that have the same scattering coefficient. A set of absorption coefficient curves is obtained by connecting adjacent points in the plot that have the same absorption coefficient. A given scattering coefficient curve shows how the absorption coefficient changes when the scattering coefficient is constant. A given absorption coefficient curve shows how the scattering coefficient changes when the absorption coefficient is constant. An example of such a calibration diagram involves plotting a function of reflectance at one distance, $R_n$ or $1/R_n$, versus a ratio such as $R_n/R_m$, where $R_n$ and $R_m$ are the reflectance values at two different distances $r_n$ and $r_m$ from the light introduction site.

A preferred method for generating the two dimensional grid comprises the step of plotting $1/R_1$ versus $R_1/R_2$. $R_1$ represents the intensity of the re-emitted light at a first collection position. This first collection position is located at a very short distance from the light introduction site. $R_2$ represents the intensity of the re-emitted light at a second collection position. This second position is also located at a very short distance from the light introduction site. The first position is adjacent to the second position. The distance of the first position from the light introduction site is not equal to the distance of the second position from the light introduction site. Thus, the first position and the second position are positions of a closely spaced pair of light collecting elements at a given light collection site. As shown schematically in FIG. 1A, light collecting elements positioned close to the light introduction site mainly collect photons scattered in the layer close to the surface of the skin and have average penetration depth between $d_{av1}$ and $d_{av2}$. A plot of $1/R_3$ versus $R_3/R_4$ yields another set of optical parameters. $R_3$ represents the intensity of re-emitted light at a third position. This third position is located at a distance farther from the light introduction site than the first and second positions. $R_4$ represents the intensity of re-emitted light at a fourth position. This fourth position is also located at a distance farther from the light introduction site than the first and second positions. The third position is adjacent to the fourth position. The distance of the third position from the light introduction site is not equal to the distance of the fourth position from the light introduction site. Thus, the third position and the fourth position are positions of a closely spaced pair of light collecting elements at a given light collection site. As shown schematically in FIG. 1A, light collecting elements at positions relatively far from the light introduction site, i. e., the third and fourth positions, collect photons scattered mainly in the deeper layers of skin and have average penetration depth between $d_{av3}$ and $d_{av4}$, respectively. Thus, re-emitted light collected by light collecting elements positioned relatively close to the light introduction site contain information mainly on the optical properties of the surface layer, which extends to a depth of a few hundred micrometers, while re-emitted light collected by light collecting elements positioned relatively far from the light introduction site contain information mainly on the optical properties of the deeper tissue layers, which extend to a depth of 1 to 2 millimeters. The optical properties of the two layers may still affect the re-emitted light from both the closer and further light collection sites and may require special mathematical treatment of the data in order to obtain values for optical parameters specific to a given layer. It should be noted that the formation of a grid is not the only means for determining optical parameters. Optical parameters can be determined from tables of values, such as, for example, tables of values stored in a computer.

The placement of the light collection sites (in the case of a single light introduction site) or the placement of the light introduction sites (in the case of a single light collection site) depends upon the number of layers in the sample and the thickness of each layer. In the case of a sample of skin tissue, the number of layers of skin and the thickness of each layer have been accurately reported in the art of dermatology.

Although the previous discussion illustrates the use of a single light introduction site and a plurality of light collection sites, it is equivalently possible to perform the same steps with other configurations of the apparatus. One such configuration comprises a single light collection site and a plurality of light introduction sites distributed at the appropriate distances from the light collection site.

In the preferred embodiment, at least two light collection sites are required in the case of a single light introduction site. It is possible to use a greater number of light collection sites than two. In an alternative embodiment, at least two light introduction sites are required in the case of a single light collection site. It is possible to use a greater number of light introduction sites than two. Increasing the number of light collection sites or light introduction sites, depending on the embodiment employed, increases the resolution of the measurement. Balance between performance and cost may determine the number of possible light introduction sites or light collection sites.

Instruments constructed according to the present invention differ from instruments of the prior art with respect to configuration. In the case of instruments of the prior art, the scattering coefficient of the tissue must be much greater than the absorption coefficient of the tissue, and the mean free path of a photon in the tissue must be much smaller than the distance between the light introduction site and the light collection sites. The wavelength range of the instruments of the present invention includes ranges where the absorption coefficient is approximately equal to the scattering coefficient, and some of the distances from the light introduction site to the light collection sites are of the same magnitude as the transport photon mean free path. Thus, a Monte Carlo simulation model is preferred to the Diffusion Theory model for calculating absorption and scattering coefficients of the tissue to process the output of the instrument of the present invention.

Determination of the concentration of an analyte in a given layer of tissue of a sample, such as, for example, a layer of skin, can be carried out by measuring the optical parameter(s) of the given layer of tissue of the sample and comparing the optical parameter(s) measured to optical parameter(s) that correspond to known concentrations of the analyte, whereby the concentration of analyte in the layer of tissue can be ascertained. The known concentrations of the analyte can be obtained by previously conducted in vivo or in vitro tests. The results of the previously conducted tests can be programmed into a data processor and used to predict concentrations of analytes by means of algorithms derived empirically.

The method and apparatus of this invention addresses the layered structure of the skin and provides solutions for the effect of outer layers of the skin on the determination of the optical properties of inner layers of the skin.

EXAMPLES

The following examples are illustrative of the apparatus and method of this invention and are not intended to be restrictive.

Example 1

Figure 2:
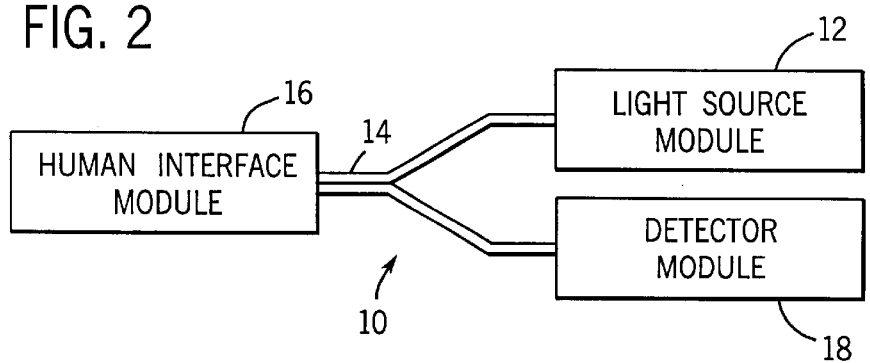
FIG. 2 is a block diagram of a device of this invention.

FIG. 2 is a block diagram illustrating an embodiment of an apparatus 10 of this invention. The apparatus 10 comprises a source of light module 12, a bifurcated optical fiber bundle 14, a human interface module 16, and a detector module 18. The source of light module 12 includes a source of modulated light (not shown), such as a Gilway L1041 lamp modulated with a Stanford Research Optical Chopper. A prism, a dichroic beam splitter, or the like (not shown) may be used to direct a portion of the beam emerging from the source of light module 12 to a reference detector (not shown), such as a Hamamatsu S-2386-44K 6C silicon detector, in order to normalize the measurements for fluctuations in intensity of the source of light. The rest of the light emerging from the source of light module 12 is focused onto the end of the source tip of a bifurcated fiber 14 by means of at least one focusing lens (not shown). Additional optical elements (not shown), such as attenuators, optical filters, and irises may be inserted between the source of light and the source tip. The source tip is preferably held in an adapter (not shown) having provisions for adjusting the location of the source tip with respect to the beam emerging from the source of light.

Figure 3A:
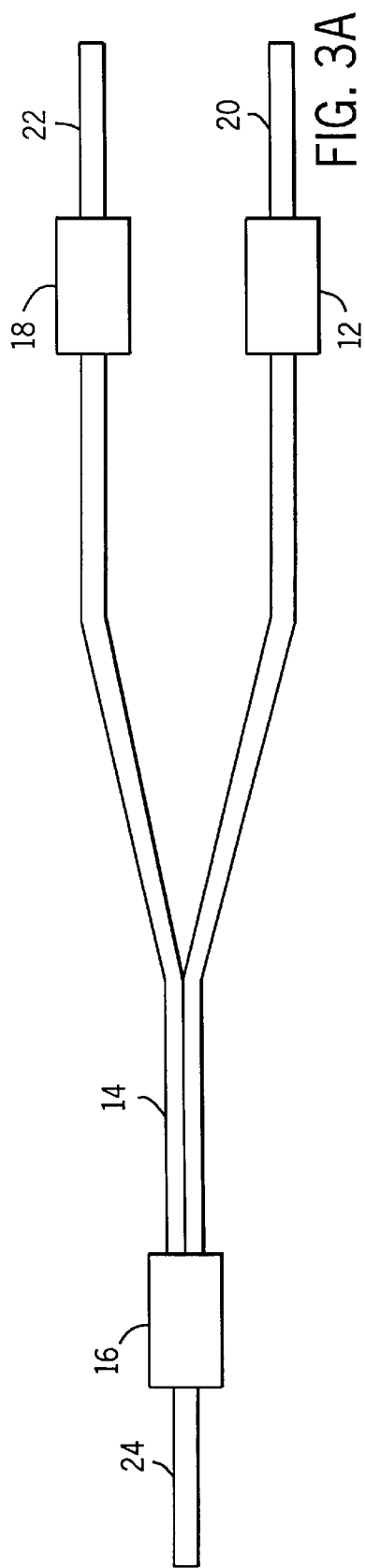
FIG. 3A is a diagram illustrating a bifurcated optical fiber bundle.
Figure 3B:
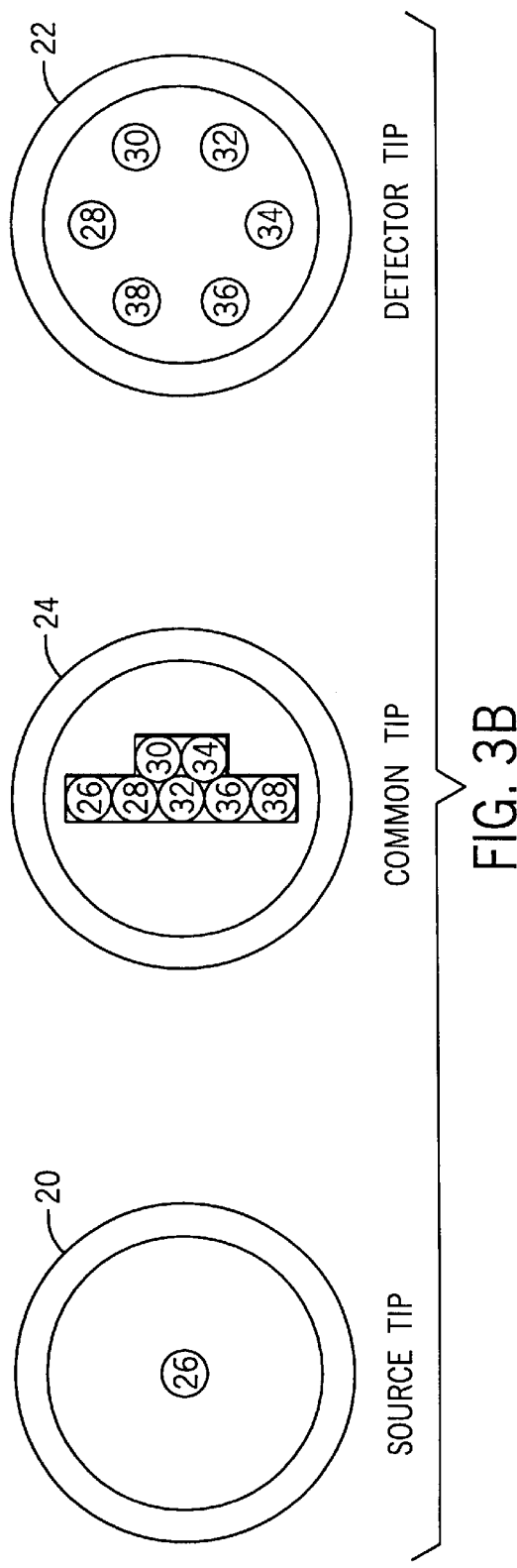
FIG. 3B is a series of diagrams showing portions of the bifurcated optical bundle of FIG. 3A.

FIGS. 3A and 3B illustrate in detail a bifurcated optical fiber bundle 14. The bifurcated optical fiber bundle 14 was constructed from Anhydrous G Low OH VIS-NIR optical fibers. Referring now to FIG. 3A, the bifurcated optical fiber bundle 14 comprises a source tip 20, a detector tip 22, and a common tip 24. The three distinct "tips" or termination sites of the bifurcated optical fiber bundle 14 are shown in FIG. 3B. During operation, the source tip 20 is contained within the source of light module 12, the detector tip 22 is contained within the detector module 18, and the common tip 24 is contained within the human interface module 16. A single optical fiber 26 transmits light from the source tip 20 to the common tip 24. Six optical fibers 28, 30, 32, 34, 36, 38 transmit light from the common tip 24 to the detector tip 22.

The common tip 24 is installed in the human interface module 16, which is placed against a body part during use. As shown in FIG. 3B, the common tip 24 comprises the fiber 26 that transmits light from the source tip 20 to the common tip 24 and the six fibers 28, 30, 32, 34, 36, 38 that collect the light that is re-emitted from the tissue sample and transmit the collected light to the detector tip 22.

Figure 4:
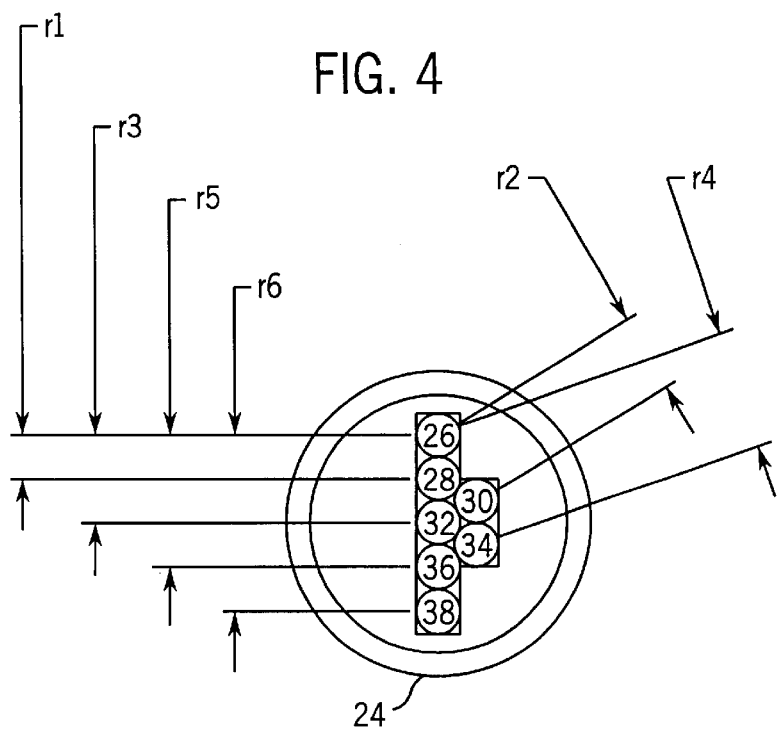
FIG. 4 is a diagram illustrating the nominal separation distances, r, between light collecting elements and the illuminating element.

One end of each of the fibers 28, 30, 32, 34, 36, 38 is located within the common tip 24 at increasing distances from the fiber 26. The nominal separation distances, r, between the center of the fiber 26 and the centers of the fibers 28, 30, 32, 34, 36, 38 of the common tip 24 are shown in FIG. 4. An important aspect of the present invention is that all of the fibers 28, 30, 32, 34, 36, 38 are located at separation distances, r, that are less than 4 mm away, and, preferably, less than 2 mm away from the fiber 26. As will be more thoroughly described below, positioning the fibers in this manner results in enhanced precision and accuracy as compared with the methods used in the prior art.

The other ends of the fibers 28, 30, 32, 34, 36, 38 are arranged in a circle within the detector tip 22, as shown in FIG. 3B, with sufficient spacing to allow a shutter to interrogate each fiber individually. The detector module 18 receives the detector tip 22 and holds it adjacent to a rotating shutter (not shown) that allows detection of the light emitted from one fiber at a time. The shutter has a detent or other means to lock it in the six fiber positions. A pair of achromatic lenses (25 mm diameter, 60 mm focal length) focuses the light from the fiber of interest on a detector. The detector was a Hamamatsu S-2386-44K 6C silicon detector. The detector module 18 also comprises appropriate electronic signal processing instrumentation, such as large dynamic range amplifiers and lock-in amplifiers. Alternatively, the outputs of the six fibers can be directed to six detectors for parallel signal processing.

Figure 5:
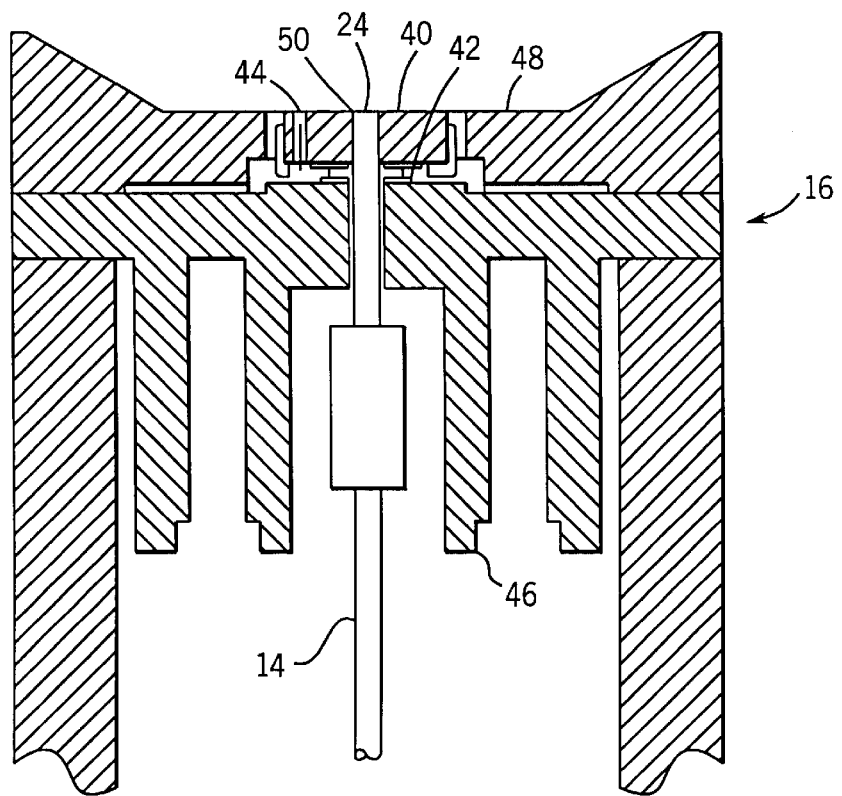
FIG. 5 is a diagram illustrating a body interface used for human volunteer experiments.

FIG. 5 illustrates the human interface module 16, which comprises an aluminum disk 40, a thermoelectric cooling element 42, a thermocouple 44, a heat sink 46, the common tip 24, and an interface adapter 48. The aluminum disk contains an aperture 50, which receives the common tip 24 of bifurcated optical fiber bundle 14 and holds the common tip 24 against a body part. The temperature of the aluminum disk 40 (and of the tissue adjacent to the disk 40) is controlled by a thermoelectric cooling element 42, such as model number SP1507-01AC (Marlow Industries). The thermoelectric cooling element 42 is powered by a temperature controller/power supply, such as model number SE5000-02 (Marlow Industries). A heat sink 46 is provided on the back of the thermoelectric cooling element 42 to enhance heat transfer. The interface adapter 48 is shaped to conform to a body part and may, for example, be cylindrical, flat, spheroidal, or any other shape.

The apparatus described in Example 1 was tested by measuring the quantity of light re-emitted from the forearms of several individuals. The distances of the light collecting elements from the light introduction site are shown in Table 1. FIG. 4 shows the spatial arrangement of the light collecting elements and the light introduction site. With a few simplifying assumptions, the values of $\mu_s'$ and $\mu_a$ for several Caucasian, Oriental, and Mediterranean subjects were determined at 34° C., by means of spatially resolved diffuse reflectance signals from all the fiber positions. The average values of $\mu_s'$ and $\mu_a$ at several illumination wavelengths were used to estimate the transport mean free path of the photons in the skin of these individuals. The results are shown in Table 2.

TABLE 1

| Light collecting element | Distance from light introduction site to light collecting element (mm) |
| --- | --- |
| $r_1$ | 0.435 |
| $r_2$ | 0.764 |
| $r_3$ | 0.899 |
| $r_4$ | 1.194 |
| $r_5$ | 1.372 |
| $r_6$ | 1.816 |

TABLE 2

Estimated Average Optical Parameters for Human Subjects

|  | 550 nm | 590 nm | 650 nm | 750 nm | 800 nm | 900 nm |
| --- | --- | --- | --- | --- | --- | --- |
| $(\mu_s' + \mu_a)$ (mm$^{-1}$) | 1.6 | 1.4 | 1.1 | 1.0 | 0.9 | 0.8 |
| Mean free path (mm) | 0.62 | 0.72 | 0.88 | 1.0 | 1.1 | 1.2 |
| Penetration depth (mm) | 0.72 | 0.92 | 1.4 | 1.7 | 1.9 | 2.0 |

Thus, the estimated mean free path is greater than the distance between the light introduction site and closest light collecting elements, while the distance between the light introduction site and the furthest light collecting elements is greater than the mean free path of photons in the tissue. The penetration depths achieved were less than or equal to about 2.0 mm. The majority of the re-emitted light was sampled at depths in the skin less than or equal to about 2 mm. Longer wavelengths, up to 2500 nm, can be selected to achieve shallower or deeper penetration depth.

Example 2

The method of this example was carried out with the apparatus described in Example 1. A suspension containing a lipids emulsion comprising 0.65% Intralipid® (a dilution of 10% I.V. Fat Emulsion, made by Pharmacia, Clayton, N.C.) in water was used. This type of suspension has been used in the art to simulate the scattering of human tissue in the near-infrared region of the electromagnetic spectrum. A volume of the suspension (45 mL) was placed in a 50 mL polypropylene centrifuge vial. The opening of the vial was sealed with a polyethylene film (15 $\mu$m thick, $\mu_a$=0, $\mu_s'$=0, Cling Wrap, Dow Chemical Company), a rubber band fixing it in place. The vial containing the suspension was inverted and placed on top of the optical fiber bundle at the human interface module 16 described in Example 1, the polyethylene film contacting the optical fiber bundle. Reflectance as a function of distance from the light introduction site was determined. Complete reflectance curves are shown in FIG. 6A for wavelength 590 nm and are designated as bulk scattering. The ratio of the re-emitted light collected by the two light collecting fibers closest to the light introduction site ($R_1/R_2$), and the ratio of the re-emitted light collected by the two light collecting fibers furthest from the light introduction site ($R_5/R_6$) are plotted in FIG. 6B. In FIG. 6B, $R_1$ is the intensity of the light re-emitted at distance $r_1$ from the illuminating fiber. $R_2$ is the intensity of the light re-emitted at distance $r_2$ from the illuminating fiber. $R_5$ is the intensity of the light re-emitted at distance $r_5$ from the illuminating fiber. $R_6$ is the intensity of the light re-emitted at distance $r_6$ from the illuminating fiber. The values of $r_1$, $r_2$, $r_5$, and $r_6$ are set forth in Table 1. The re-emitted light collected by the fibers closest to the light introduction site, $R_1$ and $R_2$, mainly represents the signal generated close to the interface of the scattering medium and the optical instrument (in this case, the polyethylene film). The re-emitted light collected by the fibers further from the light introduction site, $R_5$ and $R_6$, mainly represents the signal generated in the bulk of the scattering medium (in this case, the Intralipid® suspension).

To simulate the effect of the stratum corneum on the scattering pattern, a sheet of polyvinyl alcohol (80 micrometer thick) containing scattering hollow polystyrene particles (referred to hereinafter as PVA sheet) was added between the optical fiber bundle and the inverted covered vial. The effect of this sheet is to mimic the stratum corneum and create a layered structure where the outermost layer has absorption and scattering properties different from the bulk of the scattering medium. These polyvinyl alcohol sheets have been described in W. Steenbergen and F. deMul, "New optical tissue phantom and its use for studying laser Doppler blood flowmetry", SPIE Proceedings, Vol. 3196 (1997), pages 12–23, incorporated herein by reference. The refractive index of PVA sheet was 1.53, the thickness of the PVA sheet was 80 micrometers, the scattering centers were hollow polystyrene particles (0.8 micrometer), and the reduced scattering coefficient ranged from 4.5 mm$^{-1}$ at 590 nm to 2.6 mm$^{-1}$ at 950 nm. The effect of the scattering layer as measured at wavelength 590 nm is shown in FIG. 6A and FIG. 6B. There was a noticeable change in the reflectance of the layered phantom as a result of the added the PVA sheet. This change occurred mainly in the values of $R_1/R_2$, with a minimal change being observed in the values of $R_5/R_6$, because $R_5/R_6$ mainly represents mainly light interaction with the deeper unchanged bulk phase.

A layer of polyvinyl alcohol sheet (80 micrometer thick) containing hollow polystyrene particles was inserted between the optical fiber bundle and the first PVA sheet covering the inverted covered vial. The total thickness of the PVA sheets was 160 micrometers. Silicon oil was applied to the interfaces of the PVA sheets to assure index matching between the layers simulating the stratum corneum. The effect of the second layer of polyvinyl alcohol sheet is to mimic a stratum corneum having an increased thickness, because different body parts have different thicknesses of the stratum corneum. The effect of the scattering layer is shown in FIGS. 6A and 6B for wavelength 590 nm. There was a noticeable change in the reflectance of the layered phantom as a result of adding the second PVA sheet. There was an increase in the values of $R_1/R_2$, which mainly represents the interaction of light with the surface layer. There was a minimal change in the values of $R_5/R_6$ upon increasing the thickness of the surface layer. The $R_5/R_6$ ratio mainly represents the interaction of light with the bulk scattering medium. The magnitude of the change indicates that the change in scattering properties of the surface layer has a minimal effect on the measurement of optical properties of the bulk or the deeper layers of the scattering medium. Similar effects are observed at 900 nm as shown in FIGS. 7A and 7B. Thus, the instrument of this invention is able to track changes in the optical properties at the outer surface of a tissue-simulating phantom.

Example 3

In a manner similar to that of Example 2, the apparatus and method of this invention was tested on a tissue-simulating phantom, which comprised a suspension containing a lipids emulsion comprising 0.65% Intralipid® emulsion and 0.012% nigrosine (Eastman Kodak, Rochester, N.Y., Cat. No. C3536). A liquid phantom was constructed in the same manner as described in the first part of Example 2. Instead of the almost non-absorbing pure Intralipid® suspension used in Example 2, this blue dye solution was used to simulate both scattering and absorbing properties of human tissues. The absorption coefficients of dye-containing suspension at several measurement wavelengths are listed below.

TABLE 3

| Wavelength (nm) | $\mu_a$ (mm$^{-1}$) |
|---|---|
| 590 | 0.2710 |
| 650 | 0.2373 |
| 750 | 0.1438 |
| 800 | 0.1103 |
| 900 | 0.0669 |

In addition, to simulate the effect of the stratum corneum on the reflection pattern a PVA sheet (80 $\mu$m thick, the same as that used in Example 2) was inserted between the optical fiber bundle and the liquid phantom. Variations in the stratum corneum were further simulated by using two layers of the PVA sheet (160 $\mu$m thick), with silicon oil being applied to the interfaces of the PVA sheets to assure index matching between the layers simulating the stratum corneum.

Figure 8A:
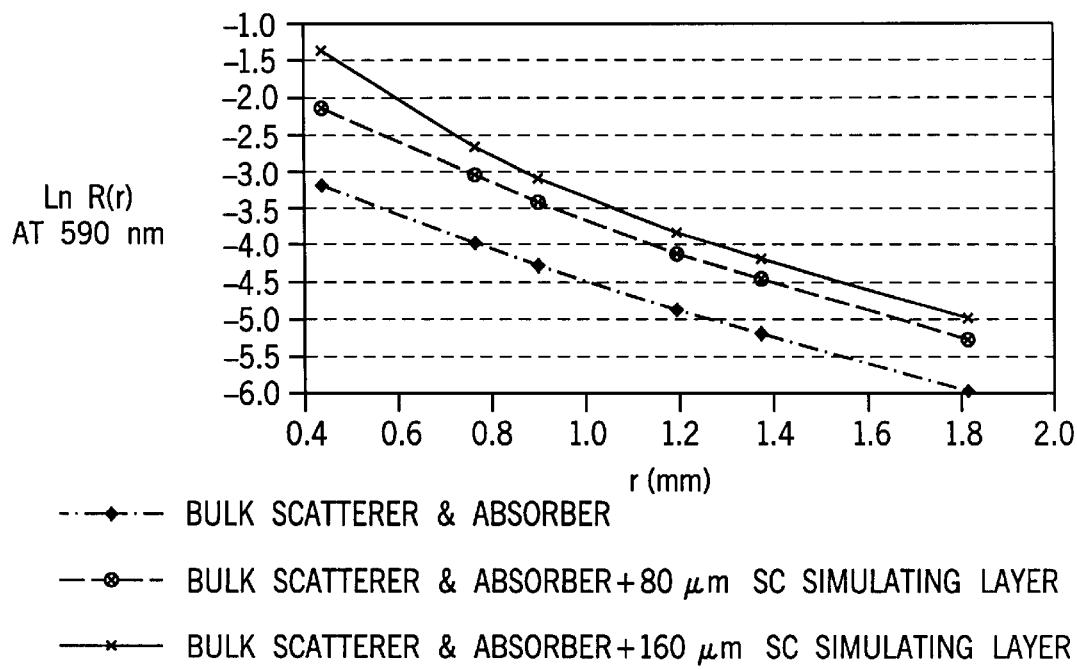
FIG. 8A is a graph illustrating the spatially resolved diffuse reflectance signal at 590 nm of a bulk scattering medium (a suspension comprising a lipids emulsion with a blue dye added) with and without layers simulating the stratum corneum.
Figure 8B:
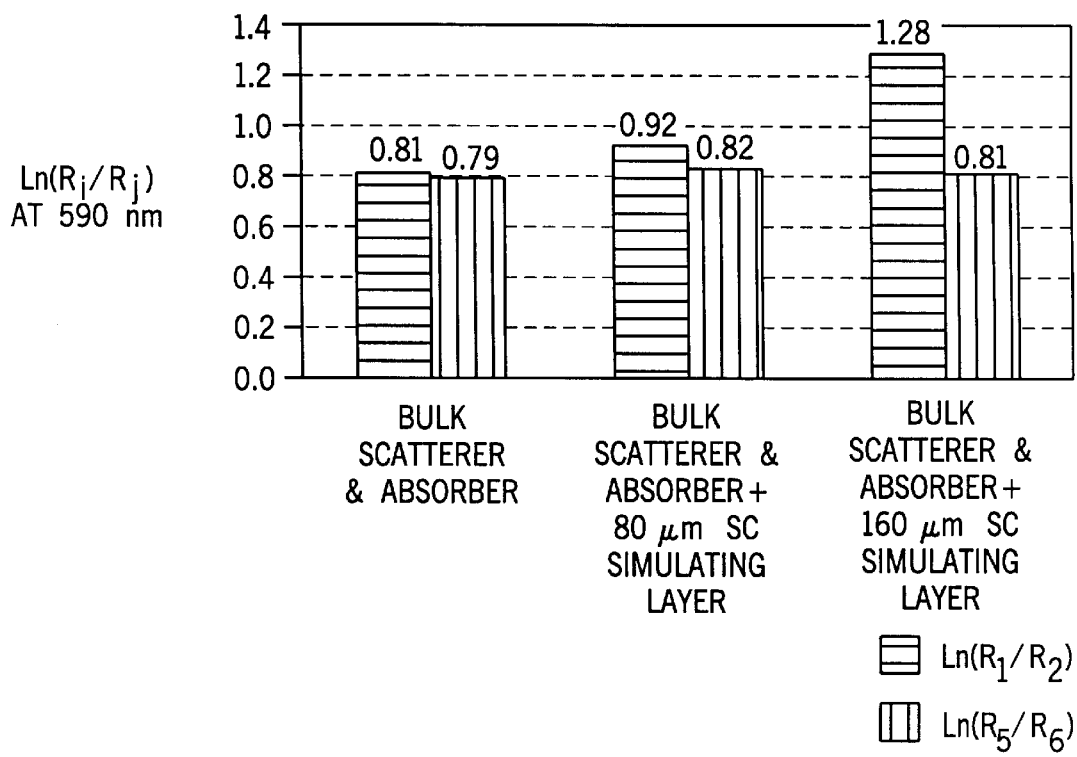
FIG. 8B is a graph illustrating the sensitivity of the slope of the 590 nm spatially resolved diffuse reflectance signal at different separations of the light introduction site from the light collection site to changes in the optical properties of a layer simulating the stratum corneum.

In spatially resolved diffused reflectance at 590 nm, a general increase in reflectance amplitude is noted when one or two layers of a sheet simulating the stratum corneum is inserted (FIG. 8A). This increase resulted from the stronger scattering and weaker absorption characteristics of the PVA sheets, when compared with those characteristics of the blue Intralipid® suspension. Moreover, the reflectance curves show noticeable changes in curvature. As a result, the slope of the curve varies greatly at the smaller distance from the light introduction site (e. g., $r_1$ and $r_2$), while remaining almost unchanged at the greater distance from the light introduction site (e. g., $r_5$ and $r_6$). The actual distances are set forth in Table 1. This phenomenon is illustrated more clearly in FIG. 8B, where the change in slope as a function of the number of PVA sheets (as represented by the Ln ($R_i/R_j$)) is depicted. It seems that the large changes in $R_1/R_2$ are greatly influenced by the changes in the topmost layer. In contrast, the minimal changes in $R_5/R_6$ represent the unchanged characteristics of the bulk part of the phantom. In other words, measurement at the smaller distances from the light introduction site $r_1$ and $r_2$ is useful for sensing the optical properties of the top layer of the phantom. This measurement is particularly useful when the contribution of the top layer to the measurement at greater distances from the light introduction site, $r_5$ and $r_6$, needs to be accounted for. This is apparent at a wavelength of 900 nm, where the difference in absorption between the top layer and the bulk part of the phantom becomes smaller; addition of the top layer to the phantom has much less effect on $R_5$, $R_6$, and $R_5/R_6$. However, very significant changes are still observed in $R_1$, $R_2$, and $R_1/R_2$, as shown in FIGS. 9A and 9B.

Example 4

The apparatus and method of this invention were tested on human volunteers. The following experiments were performed to test the effect of changing the absorption and scattering characteristics of the outer layer of skin on the spatially resolved diffuse reflectance signal, which was measured at different distances from the light introduction site. The spatially resolved diffuse reflectance signal of the inner left arm of a Caucasian volunteer was measured. Room temperature was 22° C. and temperature of the common tip 24 and aluminum disk 40 in FIG. 5 was set to 34° C. The temperature at the measurement site was allowed to equilibrate at 34° C. for two minutes before the measurement was begun. In the first part of the experiment, measurements were first made directly on the volunteer's arm, and then another measurement was made with a nearly purely absorbing layer ($\mu_s \approx 0$) inserted between the common tip 24 of the human interface module 16 and the arm. The nearly as a polyacrylic material (Pale Grey #397, ROSCO, Stamford Conn.), 64 μm thick, and having the transmittance characteristics shown below.

TABLE 4

| Wavelength (nm) | Transmittance (%) |
| --- | --- |
| 590 | 67 |
| 650 | 67 |
| 750 | 84 |
| 900 | >84 |

Figure 10A:
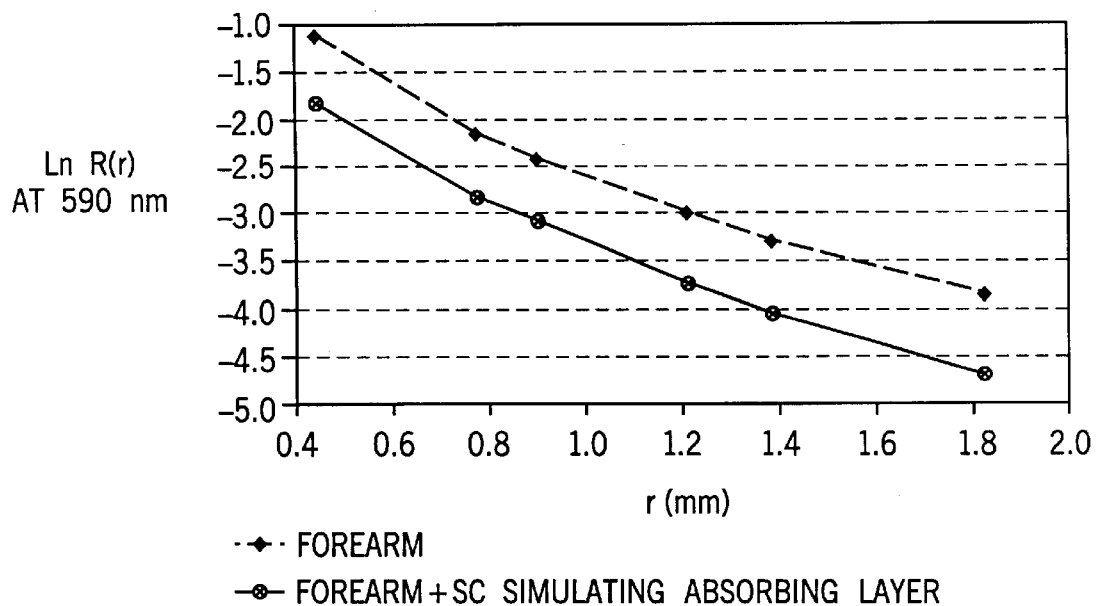
FIG. 10A is a graph illustrating the spatially resolved diffuse reflectance signal at 590 nm of a Caucasian volunteer with and without a layer simulating the stratum corneum, the layer having a dominantly absorbing property.
Figure 10B:
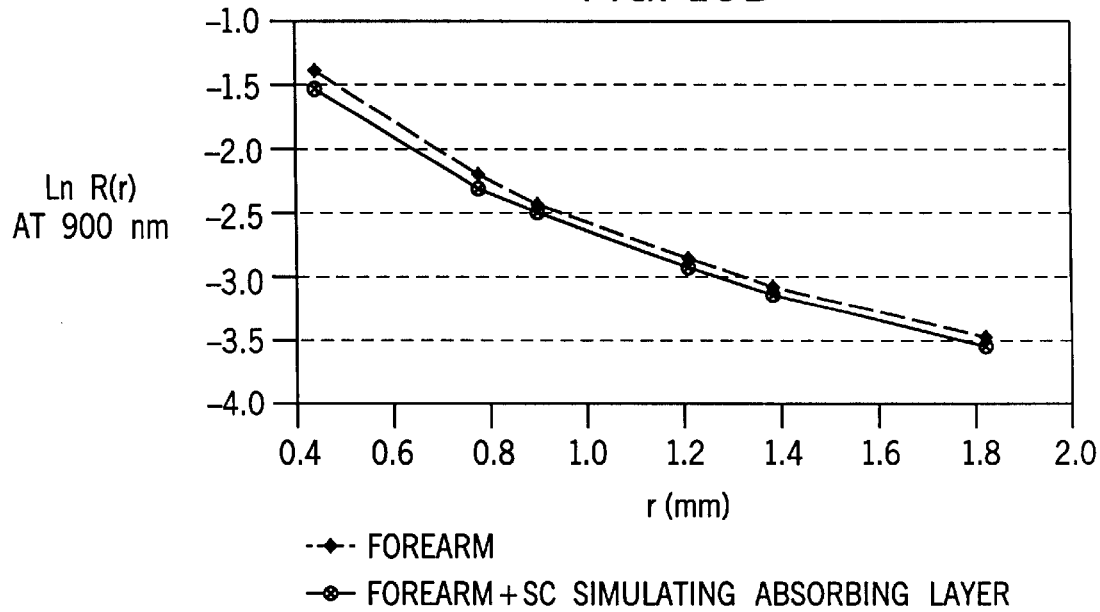
FIG. 10B is a graph illustrating the spatially resolved diffuse reflectance signal at 900 nm of a Caucasian volunteer with and without a layer simulating the stratum corneum, the layer having a dominantly absorbing property.

FIGS. 10A and 10B depict the effects of the topmost layer on the measurement of the spatially resolved diffuse reflectance signal. At the strongly absorbing wavelength 590 nm, an almost parallel downward shift of the reflectance curve can be seen (FIG. 10A). At the nearly non-absorbing wavelength 900 nm, the parallel shift is still seen, but to a very small extent (FIG. 10B). This example illustrates that the effect of absorption in the topmost layers is to shift the R(r) curve downward, i. e., there is no preferred detection position for tracking such effect.

In the second part of the experiment, measurements were first made directly on the volunteer's arm, and then another measurement was made with a nearly purely scattering layer being inserted between the arm and the optical fiber bundle of the human interface module 16. This scattering layer was a sheet of white vellum paper having a thickness of 81 μm (Cat. #3R3525, Xerox, Rochester, N.Y.).

Figure 11A:
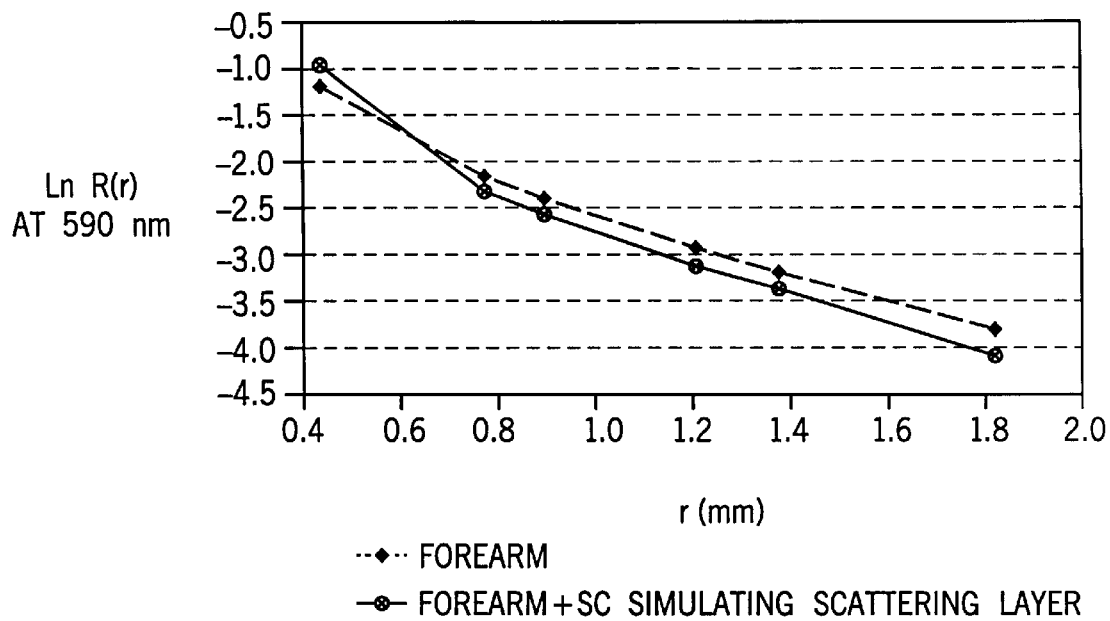
FIG. 11A is a graph illustrating the spatially resolved diffuse reflectance signal at 590 nm of a Caucasian volunteer with and without a layer simulating the stratum corneum, the layer having a dominantly scattering property.
Figure 11B:
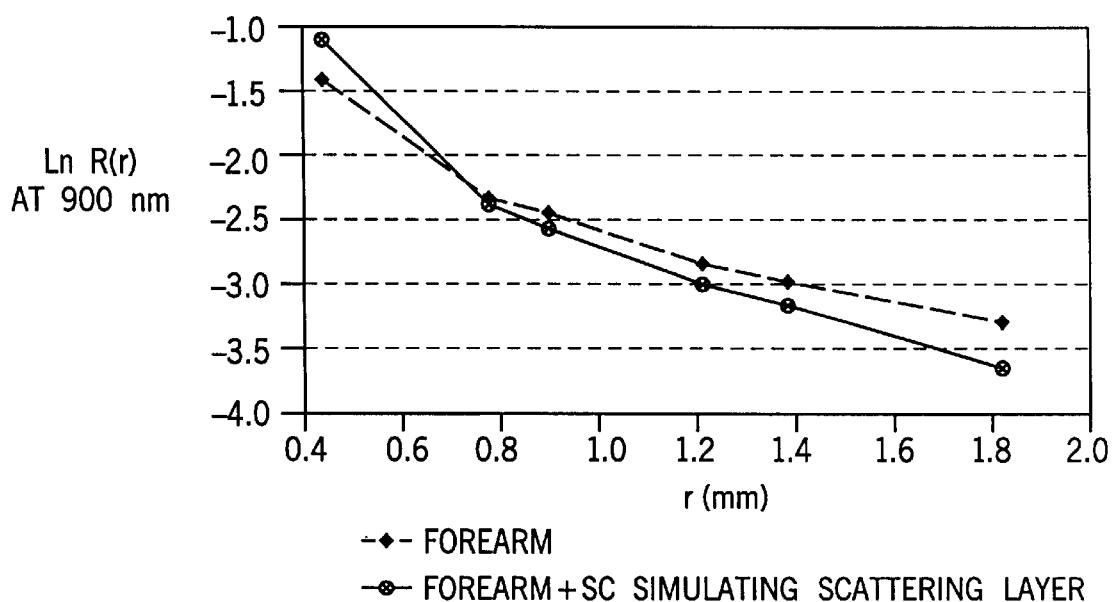
FIG. 11B is a graph illustrating the spatially resolved diffuse reflectance signal at 900 nm of a Caucasian volunteer with and without a layer simulating the stratum corneum, the layer having a dominantly scattering property.

FIGS. 11A and 11B depict the effects of the topmost layer on the measurement of the spatially resolved diffuse reflectance signal, at wavelengths 590 nm (FIG. 11A) and 900 nm (FIG. 11B). Due to the non-specificity of scattering with respect to wavelength, the effect of the top layer on the spatially resolved diffuse reflectance signal observed for both wavelengths was similar. The apparent curvature changes for the R(r) curves, which are much greater at small distances from the light introduction site, $r_1$ and $r_2$, than at greater distances from the light introduction site, $r_5$ and $r_6$, are evident. In other words, the slope of the R(r) curves at the smaller distance between the light introduction site and the light collection site ($R_1/R_2$) has changed significantly, while only minimal changes are seen for the slope of the R(r) curves at the greater distance between the light introduction site and the light collection site ($R_5/R_6$).

In the third and the last part of the experiment, measurements were first made directly on the volunteer's arm, and then another measurement was made with an absorbing and scattering layer being inserted between the arm and the optical fiber bundle of the human interface module 16. This layer was a sheet of light blue vellum paper, 71 μm thick.

FIGS. 12A and 12B depict the effects of the topmost layer on the measurement of the spatially resolved diffuse reflectance signal, at wavelengths 590 nm (FIG. 12A) and 900 nm (FIG. 12B). Due to both the absorbing and scattering characteristics of the top layer, both significant downward shift and the curvature change of the R(r) curves can be observed. The shift is much larger at the more absorbing wavelength 590 nm than at the less absorbing wavelength 900 nm. However, the curvature changes are similar at both wavelengths. Again, the slope of the R(r) curves at the smaller distance between the light introduction site and the light collection site ($R_1/R_2$) has changed significantly, while only minimal changes are seen for the R(r) curves at the greater distance between the light introduction site and the light collection site ($R_5/R_6$).

FIGS. 13A and 13B summarize the results of the experiment described above regarding the effects of inserting additional stratum corneum simulating layers between the optical fiber bundle and the human forearm. The curvature changes for the R(r) curve from the arm measurement due to higher scattering top layers mainly occur at the smaller distance between the light introduction site and the light collection site, $r_1$ and $r_2$ (0.4 to 0.8 mm). The diffuse reflectance ratio $R_1/R_2$ (which represents the slope of the R(r) curve at a small distance between the light introduction site and the light collection site) is much more sensitive than the diffuse reflectance ratio $R_5/R_6$ (which represents the slope of the R(r) curve at a greater distance between the light introduction site and the light collection site). More specifically, in terms of the sensitivity to changes in the slope of the R(r) curve from the arm measurement, it is apparent that for a nearly purely absorbing top layer (left pair of bars in FIGS. 13A and 13B), there was no discernible difference for short and long distance measurement. Measurement at short distances is preferred to measurement at long distances for a purely scattering top layer (middle pair of bars in FIGS. 13A and 13B). Measurement at short distances is preferred to measurement at long distances for a layer that has both an absorbing and scattering top layer (right pair of bars in FIGS. 13A and 13B).

Example 5

Another example of tests on human volunteers is summarized in FIGS. 14A and 14B. The following experiment was performed to test the effect of changing the absorption and scattering characteristics of the outer layer of skin on the spatially resolved diffuse reflectance signal, which was measured at different distances from the light introduction site. The spatially resolved diffuse reflectance values of the inner left arms of two Caucasian (light-skinned) volunteers and two African-American (dark-skinned) volunteers were measured. Room temperature was 22° C. and temperature of the common tip 24 and aluminum disk 40 in FIG. 5 was set to 34° C. The temperature at the measurement site was allowed to equilibrate at 34° C. for two minutes before the measurement was begun. FIG. 14A shows the spatially resolved diffuse reflectance signal for the dorsal forearm of the four volunteers at a wavelength of 560 nm. Noticeable differences in the slopes and magnitudes of the spatially resolved diffuse reflectance signal were observed for the light-skinned and dark-skinned volunteers. FIG. 14B shows the difference in the ratio $R_1/R_2$ and the ratio $R_5/R_6$ for the four subjects. The four subjects exhibited close spatially resolved diffuse reflectance ratio signals at larger distances between the light introduction site and the light collection site (mean=0.88±0.10). At smaller distances between the light introduction site and the light collection site, considerable difference was observed. The mean of the Ln ($R_1/R_2$) (which represents the slope of R(r) curve) was 1.4 for the dark-skinned subjects and 0.9 for the light-skinned subjects. Melanosomes, which are the pigment-containing particles of the skin, are known to be concentrated in the top layers of the skin. These pigmented particles have different absorption and scattering coefficients from the cells and fibers of the stratum corneum and the epidermis. It is these differences that primarily contribute to the differences in skin colors. The measurement at smaller distances between the light introduction site and the light collection site (<1 mm) carries more information about the top skin layer, including the stratum corneum and the epidermis. Conversely, the measurement at greater distances between the light introduction site and the light collection site (>1.65 mm) is less sensitive to such differences, and dominated by information about the deeper skin layer. Thus, it is possible to select a given layer within the skin structure to calculate the optical properties of the skin and determine the correct values of the absorption and scattering coefficients. Use of a signal measured only at the greater distances between the light introduction site and the light collection site would have led to erroneous values for the optical parameters for the test subjects. Also, the use of a much greater distance between the light introduction site and the light collection site would lead to a complication of mixing of optical parameters of the dermis with those of the deeper adipose and muscle layers.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the concentration of an analyte in a sample, said sample having a plurality of layers, each of said layers having different properties, said method comprising the steps of:

a) introducing a beam of light into said sample at a light introduction site on a surface of said sample;

b) determining the intensities of light re-emitted from said sample at a plurality of light collection sites on said surface of said sample, at least a first light collection site collecting light re-emitted mainly from a first layer of said sample, at least a second light collection site collecting light re-emitted mainly from a second layer of said sample, said first light collection site being at a first distance from said light introduction site, and said second light collection site being at a second distance from said light introduction site, said first distance being less than said second distance;

c) determining at least one optical parameter of said first layer of said sample;

d) determining at least one optical parameter of said second layer of said sample, said first layer having an average depth, as measured from said surface of said sample, of smaller magnitude than the average depth of said second layer, as measured from said surface of said sample; and e) determining the concentration of said analyte in said sample after said at least one optical parameter of said first layer of said sample and said at least one optical parameter of said second layer of said sample are determined by comparing said optical parameters determined in steps c) and d) with optical parameters that correspond to known concentrations of said analyte.

2. The method of claim 1, wherein light is delivered to said light introduction site by means of an optical fiber.

3. The method of claim 1, wherein the effect of interaction of said light with said first layer of said sample upon the measurement of said at least one optical parameter of said second layer of said sample is determined.

4. The method of claim 1, wherein said light has at least two wavelengths.

5. The method of claim 1, wherein said light has a wavelength ranging from about 400 nm to about 2500 nm.

6. A method for determining the concentration of an analyte in a sample, said method comprising the steps of:

a) introducing a beam of light into said sample at a light introduction site;

b) collecting light re-emitted from said sample at a plurality of light collection sites, each of said light collection sites comprising at least two light collecting elements, each of said light collection sites located at a different distance from said light introduction site;

c) determining the intensity of said light re-emitted at a first light collecting element of a light collection site located at a first distance from said light introduction site and the intensity of said light re-emitted at at least a second light collecting element of said light collection site located at said first distance from said light introduction site;

d) determining the absorption coefficient and the scattering coefficient of said sample at a given depth of said sample by means of a mathematical relationship between intensity of said light re-emitted at said first light collecting element of said light collection site located at said first distance from said light introduction site and intensity of said light re-emitted at at least a second light collecting element of said light collection site located at said first distance from said light introduction site;

e) determining the intensity of said light re-emitted at a first light collecting element of a light collection site located at a second distance from said light introduction site and the intensity of said light re-emitted at at least a second light collecting element of said light collection site located at said second distance from said light introduction site, wherein said second distance is greater than said first distance;

f) determining the absorption coefficient and the scattering coefficient of the sample at a greater depth of said sample than that of step d) by means of a mathematical relationship between intensity of said light re-emitted at said first light collecting element of said light collection site located at said second distance from said light introduction site and intensity of said light re-emitted at at least a second light collecting element of said light collection site located at said second distance from said light introduction site; and g) determining the concentration of said analyte in said sample after said absorption coefficient and said scattering coefficient of said sample at said depth in step d) and said absorption coefficient and said scattering coefficient of said sample at said depth in step f) are determined by comparing said absorption coefficients and said scattering coefficients determined in steps d) and f) with absorption coefficients and scattering coefficients that correspond to known concentrations of said analyte.

7. The method of claim 6, wherein said light collecting elements comprise optical fibers.

8. The method of claim 6, wherein said light collecting elements in any light collection site are separated by a distance equal to or less than the average transport mean free path of photons in the sample.

9. The method of claim 8, wherein said light collecting elements in any light collection site are separated by a distance of less than 1 mm.

10. The method of claim 6, wherein the distance between said light introduction site of said sample and any light collecting element is no more than 6 mm.

11. A method for determining the concentration of an analyte in a sample, said sample having a plurality of layers, each of said layers having different properties, said method comprising the steps of:

a) introducing a plurality of beams of light into said sample at a plurality of light introduction sites on a surface of said sample, a first light introduction site being at a first distance from a light collection site on said surface of said sample, a second light introduction site being at a second distance from said light collection site on said surface of said sample, said first distance being less than said second distance;

b) determining the intensities of light re-emitted from said sample at said light collection site, said light collection site collecting light re-emitted mainly from a first layer of said sample and collecting light re-emitted mainly from a second layer in said sample, said light re-emitted from said first layer being introduced at said first light introduction site, said light re-emitted from said second layer being introduced at said second light introduction site;

c) determining at least one optical parameter of a said first layer of said sample;

d) determining at least one optical parameter of said second layer of said sample, said first layer having an average depth, as measured from said surface of said sample, of smaller magnitude than the average depth of said second layer, as measured from said surface of said sample; and e) determining the concentration of said analyte in said sample after said at least one optical parameter of said first layer of said sample and said at least one optical parameter of said second layer of said sample are determined by comparing said optical parameters determined in steps c) and d) with optical parameters that correspond to known concentrations of said analyte.

12. The method of claim 11, wherein light is delivered to said light introduction sites of said sample by means of optical fibers.

13. The method of claim 11, wherein the effect of interaction of said light with said first layer of said sample upon the measurement of said at least one optical parameter of said second layer of said sample is determined.

14. The method of claim 11, wherein said light has at least two wavelengths.

15. The method of claim 11, wherein said light has a wavelength ranging from about 400 nm to about 2500 nm.

16. A method for determining the concentration of an analyte in a sample, said method comprising the steps of:

a) introducing beams of light into said sample at a plurality of light introduction sites by a plurality of groups of illuminating elements, at least two illuminating elements being at each of said light introduction sites, each of said light introduction sites located at a different distance from a light collection site;

b) collecting light re-emitted from said sample at said light collection site;

c) determining the intensity of said re-emitted light resulting from illumination by a first illuminating element of a light introduction site located at a first distance from said light collection site and the intensity of said re-emitted light resulting from illumination by at least a second illuminating element of said light introduction site located at said first distance from said light collection site;

d) determining the absorption coefficient and the scattering coefficient of said sample at a given depth in said sample by means of a mathematical relationship between intensity of said re-emitted light resulting from illumination by said first illuminating element of said light introduction site located at said first distance from said light collection site and intensity of said re-emitted light resulting from illumination by at least a second illuminating element of said light introduction site located at said first distance from said light collection site;

e) determining the intensity of said re-emitted light resulting from illumination by a first illuminating element of a light introduction site located at a second distance from said light collection site and the intensity of said re-emitted light resulting from illumination by at least a second illuminating element of said light introduction site located at said second distance from said light collection site, wherein said second distance is greater than said first distance;

f) determining the absorption coefficient and the scattering coefficient of said sample at a greater depth of said tissue than that of step d) by means of a mathematical relationship between intensity of said re-emitted light resulting from illumination by said first illuminating element of said light introduction site located at said second distance from said light collection site and intensity of said re-emitted light resulting from illumination by at least a second illuminating element of said light introduction site located at said second distance from said light collection site; and g) determining the concentration of said analyte in said sample after said absorption coefficient and said scattering coefficient of said sample at said depth in step d) and said absorption coefficient and said scattering coefficient of said sample at said depth in step f) are determined by comparing said absorption coefficients and said scattering coefficients determined in steps d) and f) with absorption coefficients and scattering coefficients that correspond to known concentrations of said analyte.

17. The method of claim 16, wherein said illuminating elements comprise optical fibers.

18. The method of claim 16, wherein said illuminating elements in any light introduction site are separated by a distance equal to or less than the mean free path of photons in said sample.

19. The method of claim 18, wherein said illuminating elements in any light introduction site are separated by a distance of less than 1 mm.

20. The method of claim 16, wherein the distance between said light collection site of said sample and any illuminating element is no more than 6 nm.

21. A method for determining the concentration of an analyte in a sample, said sample having a plurality of layers, each of said layers having different properties, said method comprising the steps of:
   a) introducing a beam of light into said sample at a light introduction site;
   b) collecting light re-emitted from said sample at a plurality of light collection sites, each of said light collection sites comprising at least two light collecting elements, each of said light collection sites located at a different distance from said light introduction site;
   c) determining the intensity of said light re-emitted at a first light collecting element of a light collection site located at a first distance from said light introduction site and the intensity of said light re-emitted at at least a second light collecting element of said light collection site located at said first distance from said light introduction site;
   d) determining the absorption coefficient and the scattering coefficient of said sample in a first layer of said sample by means of a mathematical relationship between intensity of said light re-emitted at said first light collecting element of said light collection site located at said first distance from said light introduction site and intensity of said light re-emitted at at least a second light collecting element of said light collection site located at said first distance from said light introduction site;
   e) determining the intensity of said light re-emitted at a first light collecting element of a light collection site located at a second distance from said light introduction site and the intensity of said light re-emitted at at least a second light collecting element of said light collection site located at said second distance from said light introduction site, wherein said second distance is greater than said first distance;
   f) determining the absorption coefficient and the scattering coefficient of the sample in a second layer of said sample by means of a mathematical relationship between intensity of said light re-emitted at said first light collecting element of said light collection site located at said second distance from said light introduction site and intensity of said light re-emitted at at least a second light collecting element of said light collection site located at said second distance from said light introduction site; and
   g) determining the concentration of said analyte in said sample after said absorption coefficient and said scattering coefficient of said first layer of said sample and said absorption coefficient and said scattering coefficient of said second layer of said sample are determined by comparing said absorption coefficients and said scattering coefficients determined in steps d) and f) with absorption coefficients and scattering coefficients that correspond to known concentrations of said analyte.

22. A method for determining the concentration of an analyte in a sample, said method comprising the steps of:
   a) introducing a beam of light into said sample at a light introduction site on a surface of said sample;
   b) determining the intensities of light re-emitted from said sample at a plurality of light collection sites on said surface of said sample, at least a first light collection site collecting light re-emitted mainly from a first layer of said sample, at least a second light collection site collecting light re-emitted mainly from a second layer of said sample, said first light collection site being at a first distance from said light introduction site, and said second light collection site being at a second distance from said light introduction site, said first distance being less than said second distance;
   c) determining at least one optical parameter at a given depth of said first layer of said sample;
   d) determining at least one optical parameter at a second depth of said sample, said given depth, as measured from said surface of said sample, being of smaller magnitude than said second depth, as measured from said surface of said sample; and
   e) determining the concentration of said analyte in said sample after said at least one optical parameter of said given depth of said sample and said at least one optical parameter of said second depth of said sample are determined by comparing said optical parameters determined in steps c) and d) with optical parameters that correspond to known concentrations of said analyte.

23. A method for determining the concentration of an analyte in a sample, said sample having a plurality of layers, each of said layers having different properties, said method comprising the steps of:
   a) introducing beams of light into said sample at a plurality of light introduction sites by a plurality of groups of illuminating elements, at least two illuminating elements being at each of said light introduction sites, each of said light introduction sites located at a different distance from a light collection site;
   b) collecting light re-emitted from said sample at said light collection site;
   c) determining the intensity of said re-emitted light resulting from illumination by a first illuminating element of a light introduction site located at a first distance from said light collection site and the intensity of said re-emitted light resulting from illumination by at least a second illuminating element of said light introduction site located at said first distance from said light collection site;
   d) determining the absorption coefficient and the scattering coefficient of said sample in a first layer of said sample by means of a mathematical relationship between intensity of said re-emitted light resulting from illumination by said first illuminating element of said light introduction site located at said first distance from said light collection site and intensity of said re-emitted light resulting from illumination by at least a second illuminating element of said light introduction site located at said first distance from said light collection site;
   e) determining the intensity of said re-emitted light resulting from illumination by a first illuminating element of a light introduction site located at a second distance from said light collection site and the intensity of said re-emitted light resulting from illumination by at least a second illuminating element of said light introduction site located at said second distance from said light collection site, wherein said second distance is greater than said first distance;

f) determining the absorption coefficient and the scattering coefficient of said sample in a second layer of said sample by means of a mathematical relationship between intensity of said re-emitted light resulting from illumination by said first illuminating element of said light introduction site located at said second distance from said light collection site and intensity of said re-emitted light resulting from illumination by at least a second illuminating element of said light introduction site located at said second distance from said light collection site; and g) determining the concentration of said analyte in said sample after said absorption coefficient and said scattering coefficient of said first layer of said sample and said absorption coefficient and said scattering coefficient of said second layer of said sample are determined by comparing said absorption coefficients and said scattering coefficients determined in steps d) and f) with absorption coefficients and scattering coefficients that correspond to known concentrations of said analyte.

24. A method for determining the concentration of an analyte in a sample, said method comprising the steps of:

a) introducing a plurality of beams of light into said sample at a plurality of light introduction sites on a surface of said sample, a first light introduction site being at a first distance from a light collection site on said surface of said sample, a second light introduction site being at a second distance from said light collection site on said surface of said sample, said first distance being less than said second distance;

b) determining the intensities of light re-emitted from said sample at said light collection site, said light collection site collecting light re-emitted mainly from a first layer of said sample and collecting light re-emitted mainly from a second layer in said sample, said light re-emitted from said first layer being introduced at said first light introduction site, said light re-emitted from said second layer being introduced at said second light introduction site;

c) determining at least one optical parameter at a given depth of said sample;

d) determining at least one optical parameter at a second depth of said sample, said given depth, as measured from said surface of said sample, of smaller magnitude than the second depth, as measured from said surface of said sample; and e) determining the concentration of said analyte in said sample after said at least one optical parameter of said given depth of said sample and said at least one optical parameter of said second depth of said sample are determined by comparing said optical parameters determined in steps c) and d) with optical parameters that correspond to known concentrations of said analyte.

* * * * *